United States Patent [19]

Ghiasi et al.

[11] Patent Number: 5,955,088
[45] Date of Patent: Sep. 21, 1999

[54] PHARMACEUTICAL COMPSITION OF HERPES SIMPLEX VIRUS TYPE-1 (HSV-1), GLYCOPROTEINS

[75] Inventors: Homayan Ghiasi, Los Angeles; Anthony B. Nesburn, Malibu; Steven L. Wechsler, Westlake Village, all of Calif.

[73] Assignee: Cedars-Sinai Medical Center, Los Angeles, Calif.

[21] Appl. No.: 08/482,105

[22] Filed: Jun. 7, 1995

Related U.S. Application Data

[63] Continuation-in-part of application No. 07/829,947, Feb. 3, 1992, Pat. No. 5,679,348, application No. 08/310,370, Sep. 22, 1994, Pat. No. 5,672,349, and application No. 08/353,948, Dec. 9, 1994, Pat. No. 5,632,992, which is a continuation of application No. 07/845,920, Mar. 4, 1992, abandoned, which is a continuation-in-part of application No. 07/829,947, said application No. 08/310,370, is a continuation of application No. 07/852,999, Mar. 18, 1992, abandoned, which is a continuation-in-part of application No. 07/829,947.

[51] Int. Cl.$^6$ ............................................. A61K 39/245
[52] U.S. Cl. ............................ 424/231.1; 435/235.1; 435/69.3; 935/65
[58] Field of Search ......................... 435/69.3, 69.1, 435/91.32, 91.4, 320.1, 240.3, 235.1, 172.3; 424/130.1, 231.1; 514/935, 65

[56] References Cited

U.S. PATENT DOCUMENTS

| | | | |
|---|---|---|---|
| 4,317,811 | 3/1982 | Bertland et al. | 424/89 |
| 4,374,127 | 2/1983 | Larson et al. | 424/89 |
| 4,859,587 | 8/1989 | Roizman | 435/69.3 |
| 4,891,315 | 1/1990 | Watson et al. | 435/69.3 |
| 5,171,568 | 12/1992 | Burke et al. | 424/89 |
| 5,244,792 | 9/1993 | Burke et al. | 435/69.3 |

FOREIGN PATENT DOCUMENTS

| | | |
|---|---|---|
| 0 243 155 | 10/1987 | European Pat. Off. . |
| 0243155 | 10/1987 | European Pat. Off. . |
| 0 297 924 | 1/1989 | European Pat. Off. . |
| 0297924 | 1/1989 | European Pat. Off. . |
| 85/04587 | 10/1985 | WIPO . |
| WO85/04587 | 10/1985 | WIPO . |

OTHER PUBLICATIONS

Stranberry et al, The J. of Infectious Diseases, 1987, vol. 155 (5), pp. 914–920.
Jennings et al, 1988, Arch Virol. , vol. 98, pp. 137–153.
Erturk et al, 1989, Vaccine, vol. 7, pp. 431–436.
Abbott et al., Adrenergic Induction of HSV–1 Ocular Shedding in Rabbits. J. Ocular Pharm., 2(1):41–54 (1986).
Ashley, Personal communication (1990).
Berman et al., Efficacy of Recombinant Glycoprotein D Subunit Vaccines on the Development of Primary, Recurrent, and Latent Genital Infections with Herpes Simplex Virus Type 2 in Guinea Pigs. J. Infec. Dis., 157(5):897–902 (1988).

Blacklaws et al., Immunogenicity of herpes simplex type 1 glycoproteins expressed in vaccinia virus recombinants. Virology, 177:727–736 (1990).
Borenstein et al., Immunization of rabbits with recombinant treponema palladium Surface Antigen 4D alters the course of experimental syphilis. J. Immunol., 140:2415–2421 (1988).
Centifanto–Fitzgerald et al., Herpes Simplex Virus Latency in the Rabbit Trigeminal Ganglia: Ganglionic Superinfection (42064). Proc. Soc. Experimental Biology and Medicine, 179:55–67 (1985).
Demangone et al., Effects of acyclovir therapy during simultaneous reactivation of latent HSV–1 in rabbits. Antiviral Research, 7:237–243 (1987).
Frenkel et al., A randomized double blind, placebo–controlled phase 1 trial of a herpes simplex virus purified glycoprotein (gD1) vaccine. Interscience Con. on Antimicrobial Agents & Chemo., 206 (1990).
Ghiasi et al., Baculovirus Expressed Glycoprotein E (gE) of Herpes Simplex Virus Type 1 (HSV–1) Protects Mice against Lethal Intraperitoneal and Lethal Ocular HSV–1 Challenge. Virology, 188:469–476 (1992).
Ghiasi et al., Baculovirus–Expressed Glycoprotein G of Herpes Simplex Virus Type 1 Partially Protects Vaccinated Mice against Lethal HSV–1 Challenge. Virology, 190:233–239 (1992).
Ghiasi et al., Baculovirus expressed herpes simplex type 1 glycoprotein C protects mice from lethal HSV–1 infection. Antiviral Research, 18:291–302 (1992).
Ghiasi et al., Cell surface expression of herpes simplex virus type 1 glycoprotein H in recombinant baculovirus infected cells. Virology, 185:187–194 (1991).
Ghiasi et al., Expression of herpes simplex virus type 1 glycoprotein B in insect cells: Initial analysis of its biochemical and immunological properties. Virus Research, 22:25–39 (1991).
Ghiasi et al., Expression of Herpes Simplex Virus Type 1 Glycoprotein I in Baculovirus: Preliminary Biochemical Characterization and Protection Studies. J. Virol., 66:2505–2509 (1992).
Ghiasi et al., Expression of Seven Herpes Simplex Virus Type 1 Glycoproteins (gB, gC, gD, gG, gH, and gI): Comparative Protection against Lethal Challenge in Mice. J. Virology, 68(4):2118–2126 (1994).

(List continued on next page.)

Primary Examiner—Mary E. Mosher
Assistant Examiner—Ali R. Salimi
Attorney, Agent, or Firm—Lyon & Lyon LLP

[57] ABSTRACT

The present invention relates to the field of infectious diseases and ophthalmology. More particularly, the invention relates to compositions and methods for vaccination against Herpes Simplex Virus which rely on preparations comprising a mixture of five, six, or seven HSV glycoproteins selected from the group consisting of gB, gC, gD, gE, gG, gH, and gI.

12 Claims, 6 Drawing Sheets

OTHER PUBLICATIONS

Ghiasi et al., High level expression of each of the seven herpes simplex virus glycoproteins in insect cells using baculovirus expression vectors: subsequent use as vaccines. Invest. Ophthalmol. Visual Sci., vol. 32, No. 4, p. 806 (1991) Abstract 686.

Ghiasi et al., Immunoselection of recombinant baculovirus expressing high levels of biologically active herpes simplex virus type 1 glycoprotein D. Arch. Virol., 121:163–178 (1991).

Goldstein et al., Factor(s) present in herpes simplex virus type 1 infected cells can compensate for the loss of the large subunit of the viral ribonucleotide reductase: Characterization of an ICP6 deletion mutant. Virology, 166:41–51 (1988).

Gompels et al., The Properties and Sequence of Glycoprotein H of Herpes Simplex Virus Type 1. Virology, 153:230–247 (1986).

Green et al., Study of HSV–1 DNA species from trigeminal ganglia of rabbits during acute and latent infections. Current Eye Research, 6(1):85–89 (1987).

Harrild, Humoral response to herpes simplex virus infection. In: *The Herpesviruses,* edited by Roizman, B., New York, Plenum Press, pp. 69–86 (1985).

Hill et al., Lack of Efficacy of Adenosine–5'–Monophosphate Against HSV–1 Ocular Shedding in Rabbits. J. Ocular Pharm., 3(1):31–38 (1987).

Hill et al., Timolol Induces HSV–1 Ocular Shedding in the Latently Infected Rabbit. Invest. Ophthalmol. & Visual Sci., 28:585–590 (1987).

Inumaru et al., Expression of bluetongue virus group specific antigen VP3 in insect cells by a baculovirus vector: Its use for the detection of bluetongue virus antibodies. J. Gen. Virol., 68:1627–1635 (1987).

Jarvis et al., Glycosylation and secretion of human tissue plasminogen activator in recombinant baculovirus infected insect cells. Mol. Cell. Biol., 9:214–223 (1989).

Johnson et al., Identification of a Novel Herpes Simplex Virus Type 1 induced glycoprotein which complexes with gE and binds immunoglobulin. J. Virol., 61: 2208–2216 (1987).

Kern et al., Vaccine Therapy in Recurrent Herpes Simplex. Arch. Derm., 89:844–845 (1964).

Kino et al., Immunogenicity of herpes simplex virus glycoprotein gB–1–related protein produced in yeast. Vaccine, 7:155–160.

Kino et al., Immunogenicity of Purified Glycoprotein gB of Herpes Simplex Virus. Archives of Virology, 89:69–80 (1986).

Klein, Reinfections and site–specific immunity in herpes simplex virus infections. Vaccine, 7:380–381 (1989).

Krishna et al., Expression of glycoprotein D of herpes simplex virus type 1 in a Recombinant Baculovirus: Protective Responses and T Cell Recognition of the Recombinant–infected Cell Extracts. J. Gen. Virol., 70:1805–1814 (1989).

Kuroda et al., The Oligosaccharides of Influenza Virus Hemagglutinin Expressed in Insect Cells by a Baculovirus Vector. Virology, 174:418–429 (1990).

Laemmli, Cleavage of structural proteins during the assembly of the head of bacteriophage T4. Nature, 227:680–685 (1970).

Lee et al., Location of the structural genes for glycoproteins gD and gE and for other polypeptides in the S component of herpes simplex virus type 1 DNA. J. Virol., 43:41–49 (1982).

Maeda, Expression of Foreign Genes in Insects Using Baculovirus Vectors. Ann. Rev. Entomol. 34:351–372 (1989).

Mathews et al., Synthesis and processing glycoprotein D of herpes simplex virus types 1 and 2 in an in vitro system. J. Virol., 48:521–553 (1983).

Matsuura et al., Baculovirus expression vectors: The requirements for high level expression of proteins, including glycoproteins. J. Gen. Virol., 68:1233–1250 (1987).

McGeoch et al., The Complete DNA Sequence of the Long Unique Region in the Genome of Herpes Simplex Virus Type 1. J. gen. Virol. 69:1531–1574 (1988).

Mishkin et al., Native herpes simplex virus glycoprotein D vaccine: immunogenicity and protection in animal models. Vaccine, 9:147–153 (1991).

Morein et al., Iscom, a novel structure for antigenic presentation of membrane proteins from enveloped viruses. Nature, 308:457–460 (1984).

Nesburn et al., Efficacy and safety of therapeutic systemic HSV vaccines in the rabbit ocular recurrence model. Invest. Ophthalmol. Visual Sci., vol. 32, No. 4, p. 854 (1991) Abstract 917.

Nesburn et al., Isolation of herpes simplex virus: Isolation from rabbit trigeminal ganglia between episodes of recurrent ocular infection. Arch. Ophthalmol., 88:412–417 (1972).

Nesburn et al., Ocular safety and efficacy of an HSV–1 gD vaccine during primary and latent infection. Invest. Ophthalmol. Vis. Sci., 31:77–82 (1990).

Nesburn, Report of the corneal disease panel: Vision Research: A national plan 1983–1987. vol. II, part III, edited by Nesburn, A.B., St. Louis, MO.

O'Brien, Herpetic Eye Diseases in Animals as Models for Therapeutic Studies of Acute and Latent Herpesvirus Infections. In: *Herpesvirus,* edited by Rapp, F., New York, Alan R. Liss, Inc., pp. 101–120 (1984).

Pass et al., Identification of Patients With Increased Risk of Infection with Herpes Simplex Virus After Renal Transplantation. J. Infec. Dis., 140(4): 487–492 (1979).

Rock et al., Detection of latency related viral RNAs in trigeminal ganglia of rabbits latently infected with herpes simplex virus type 1. J. Virol., 61:3820–3826 (1987).

Sarminto et al., Membrane proteins specified by herpes simplex virus III. Role of glycoprotein VP7 (B2) in virion infectivity. J. Virol. 29:1149–1158 (1979).

Shimormura et al., Shedding by iontophoresis of 6–hydroxdopamine followed by topical epinephrine. Invest. Ophthalmol., 24:1588–1590 (1983).

Spear, Glycoproteins specified by herpes simplex virus. In: *The Herpesviruses,* edited by Roizman, B., New York, Plenum Press, pp. 315–356 (1985).

Stanberry et al., Herpes simplex virus glycoprotein treatment of recurrent genital herpes. J. Infec. Dis., 157:156–163 (1988).

Stanberry et al., Heterologous Versus Homologous Herpes Simplex Virus Glycoprotein Immunotherapy of Recurrent Genital Herpes. Pediatr. Res., 25:191A, Part 2 (1989).

Summers et al., A manual of methods for baculovirus vectors and insect cell culture procedures. Micro Gene Sys., New Haven (1988).

Takedara et al., Co–expression of the Hepatitis B surface and core antigens using baculovirus multiple expression vectors. J. Gen. Virol., 69:2763–2777 (1988).

Towbin et al., Electrophoretic transfer of proteins from polyacrylamide gels to nitrocellulose sheets: procedures and some applications. Proc. Natl. Acad. Sci., 76:4350–4354 (1979).

Atherton, Protection from retinal necrosis by passive transfer of monoclonal antibody specific for herpes simplex virus glycoprotein D, Current Eye Research 11(1):45–52 (1992).

Foster et al., "Immunomodulation of experimental murine herpes simplex keratitis: II. Glycoprotein D. Protection," Current Eye Research 7(11):1051–1061 (1988).

Ghiasi et al., "High level expression of each of the seven herpes simplex virus glycoproteins in insect cells using baculovirus expression vectors: subsequent use as vaccines," Invest. Ophthalmol. Visual Sci., 32(4):806 (1991).

Ghiasi et al., "Expression of herpes simplex virus type 1 glycoprotein B in insect cells," Virus Research 22:25–39 (1991).

Ghiasi et al., "Immunoselection of recombinant baculoviruses expression high levels of biologically active herpes simplex virus type 1 glycoprotein D," Arch. Virol. 121:163–178 (1991).

Kino et al., "Immunogenicity of herpes simplex virus glycoprotein gB–1–related protein produced in yeast," Vaccine 7:155–160 (1989).

Lausch et al., "Prevention of Herpes Keratitis by Monoclonal Antibodies Specific for Discontinuous and Continuous Epitopes in Glycoprotein D," Invest. Ophthalmol. Visual Sci., 32(10):2735–2740 (1991).

Matsuura et al., "Baculovirus Expression Vectors: the Requirements for High Level Expression of Proteins, Including Glycoproteins," J. Gen. Virol. 68:1233–1250 (1987).

Nesburn et al., "Efficacy and Safety of 'Therapeutic' Systemic HSV Vaccines in the Rabbit Ocular Recurrence Model," Abstract 917–11:30, Invest. Ophthalmol. Visual Sci. 32(4):854 (1991).

Nesburn et al., "Ocular Safety and Efficacy of an HSV–1 gD Vaccine During Primary and Latent Infection," Invest. Ophthalmol. Visual Sci. 31(8):1497–1502 (1990).

Stanberry et al., "Herpes Simplex Virus Glycoprotein Treatment of Recurrent Genital Herpes," The Journal of Infectious Diseases 157(1):156–163 (1988).

Meignier, B., Longnecker, R., and Roizman, B. "Construction and In Vivo Evaluation of Two Genetically Engineered Prototypes of Live Attenuated Herpes Simplex Virus Vaccines", Chanock, R.M. et al. (Ed.), *Vaccines 87—Modern Approaches to New Vaccines: Prevention of Aids and Other Viral, Bacterial, and Parasitic Diseases,* Cold Spring Harbor Conference, Cold Spring Harbor, New York, USA (1987): 368–373.

Erturk, M., Jennings, R., Phillpotts, R.J., and Potter, C.W., "Biochemical Characterization of Herpes Simplex Virus Type–1–Immunostimulating Complexes (ISCOMs): A Multi–Glycoprotein Structure", *Vaccine,* vol. 9, No. 9 (Sep. 1991): 668–674.

Erturk, M., Jennings, R., Hockley, D., and Potter, C.W., "Antibody Responses and Protection in Mice Immunized with Herpes Simplex Virus Type 1 Antigen Immune–stimulating complex Preparations", *Journal Gen. Virol.,* vol. 70, No. 8 (Aug. 1989): 2149–2155.

Ghiasi, H., Kaiwar, R., Nesburn, A.B., Slanina, S., and Wechsler, S.L., "Expression of Seven Herpes Simplex Virus Type 1 Glycoproteins (gB, gC, gD, gE, gH, and gI): Comparative Protection against Lethal Challenge in Mice", *Journal of Virology,* vol. 68, No. 4 (Apr. 1987): 2118–2126.

Ghiasi, H., Nesburn, A.B., and Wechsler, S.L., "Protection Against HSV–1 Induced Eye Disease by Vaccination with 7 Individually Expressed HSV–1 Glycoproteins", *Investigative Opthalmology & Visual Science,* vol. 36, No. 4 (Mar. 1995): S147.

Meignier et al., *Virology* 162:251–254 (1988).

Meignier et al., *The Journal of Infectious Diseases* 158(3):602–614 (1988).

Meignier et al., *The Journal of Infectious Diseases* 155(5):921–930 (1987).

Sanchez–Martinez et al. 1991, Virology, vol. 182, pp. 229–238.

Straus, S. et al, (1985); Annals of Internal Medicine, vol. 103 pp. 404–419.

Luckow, V. et al, 1988, Biotech., vol. 6, pp. 47–55.

PHARMACEUTICAL COMPSITION OF HERPES SIMPLEX VIRUS TYPE-1 (HSV-1), GLYCOPROTEINS

This application is a continuation-in-part of U.S. application Ser. No. 07/829,947, filed Feb. 3, 1992, now U.S. Pat. No. 5,679,348. This application is also a continuation-in-part of U.S. application Ser. No. 08/310,370, filed Sep. 22, 1994, now U.S. Pat. No. 5,672,349, which is in turn a continuation of U.S. application Ser. No. 07/852,999, Mar. 18, 1992, now abandoned, which is in turn a continuation-in-part of U.S. application Ser. No. 07/829,947, filed Feb. 3, 1992, now U.S. Pat. No. 5,679,348. The present application is also a continuation-in-part of U.S. application Ser. No. 08/353,948, filed Dec. 9, 1994, now U.S. Pat. No. 5,632,992, which is in turn a continuation of U.S. application Ser. No. 07/845,920, filed Mar. 4, 1992, now abandoned, which is in turn a continuation-in-part of U.S. application Ser. No. 07/829,947, filed Feb. 3, 1992, now U.S. Pat. No. 5,679,348. All of the above-identified parent applications are expressly incorporated herein by reference.

FIELD OF THE INVENTION

The present invention relates to the field of infectious diseases and ophthalmology. More particularly, the invention relates to compositions and methods for vaccination against Herpes Simplex Virus which rely on preparations comprising a mixture of five, six, or seven HSV glycoproteins selected from the group consisting of gB, gC, gD, gE, gG, gH, and gI.

BACKGROUND OF THE INVENTION

A. Incidence and Course of HSV Infection

Herpes Simplex Virus (HSV), also known as *herpesvirus hominis,* is classified into two (2) types, 1 and 2. HSV-1 is transmitted by physical contact, such as kissing, and is thus spread among family members and friends. About half of all babies in the United States are born with IgG antibodies to this agent which is transmitted across the placenta. As this immunity dissipates, new infections are acquired until, by age 45, close to 70% of people have become serologically positive—most without ever experiencing signs of disease, others after one or several episodes of fever blisters or cold sores.

In contrast, HSV-2, also called genital herpes, is transmitted during birth or by sexual contact. The latter's incidence rises with the number of sexual partners and has therefore greatly increased in today's society. Compared with HSV-1, genital herpes is less prevalent overall but is likewise cumulative with age. In addition, genital herpes has engendered considerable anxiety because there is tenuous evidence that it may contribute to the causation of cervical cancer, and because of the risk of vertical transmission during childbirth inducing serious disease. Infections with both causative agents are difficult to prevent; and there is as yet no proven vaccine for the prophylaxis of genital herpes. Moreover, an ocular vaccine for the prophylaxis of ocular HSV has not been tried in humans.

Turning specifically to HSV-1, it is the most common infectious cause of blindness in industrial nations. Nesburn, A. B., *Report of the corneal disease panel: Vision Research: A national plan* 1983–1987. Vol. II, part III, edited by Nesburn, A. B., St. Louis, Mo. The often prolonged ocular disease results in considerable visual morbidity, medical expense and loss of productivity in otherwise healthy individuals. Approximately 500,000 cases of ocular HSV-1 are diagnosed annually in the United States alone; and 25% to 45% of these cases may be expected to recur within 1 to 2 years after the primary disease episode. Nesburn, A. B., *Report of the corneal disease panel: Vision Research: A national plan* 1983–1987. Vol. II, part III, edited by Nesburn, A. B., St. Louis, Mo. Of note, the majority of cases diagnosed as primary HSV are actually recurrent infections, as the patient may not recall the antecedent attack. Recurrence is therefore the hallmark of HSV infection.

Following primary infection with herpes simplex virus, the virus establishes a life long latent infection in sensory nerves. At various times during the life of the latently infected individual, the virus may reactivate, travel back to the original peripheral site of infection, and produce recurrent disease. It is these repeated recurrent infections that are responsible for the vast majority of clinically important herpes simplex infections. Therefore, in addition to reducing the incidence and severity of primary infection, an ideal herpes vaccine should also prevent the establishment of latency, thereby eliminating recurrent disease.

After primary HSV infection occurs, the virus can travel in the nerves to the neurons in the trigeminal ganglia, where it then persists throughout life. This critical factor presently makes the herpes simplex infection an incurable disease, since the virus eventually may travel back down these nerves and reinfect the part of the body innervated by that nerve. Various trigger mechanisms such as trauma, fever, sunlight exposure or stress may initiate the reactivation process. This latency-reactivation-recurrence cycle results in ocular virus shedding despite a good local ocular IgA response to the virus. Klein, R. J., Reinfections and site-specific immunity in herpes simplex virus infections. *Vaccine,* 7:380–381 (1989). Once HSV has recurred in the eye, corneal disease and stromal scarring can follow, resulting in corneal blindness. Over 1,000 corneal transplants per year are currently performed in the U.S. as a direct result of HSV scarring. Hence, on recovering from the initial HSV infection, the stage is set for reinfection from one's own herpes virus for the remainder of the individual's life.

Since recurrences continue throughout the lifetime of the infected individual, it is clear that natural HSV infection affords insufficient protection against HSV recurrences. Moreover, individuals infected with one HSV serotype are only partially protected against subsequent infection with the other serotype; while individuals with non-ocular HSV-1 are not protected against subsequent ocular HSV-1 infection. Virus from a recurrent lesion on the body can be transferred to the eye, which is thought by some to be a common mode of contracting ocular infections. Because repeated recurrences of HSV do not elicit an immune response that prevents additional recurrences, there is a critical need to elicit a stronger, or perhaps a different immune response than that elicited by natural HSV-1 infection.

With further regard to immune protection, it appears that both antibody and cell-mediated immunity (CMI) are important in the control of HSV infection (Stanberry, L. R. et al., Herpes simplex virus glycoprotein treatment of recurrent genital herpes. *J. Infec. Dis.,* 157:156–63 (1988); Kern, A. B. et al., Vaccine Therapy in Recurrent Herpes Simplex, *Arch. Derm.,* 89:844–845 (1964); and Frenkel, L. et al., A randomized double blind, placebo-controlled phase 1 trial of a herpes simplex virus purified glycoprotein (gD1) vaccine. *Interscience Conf. on Antimicrobial Agents & Chemo.,* 206 (1990), incorporated herein by reference), although CMI may play a larger role. Patients with defects in CMI generally have more severe infection than those with impaired humoral immunity (Berman, P. W. et al., Efficacy of Recombinant Glycoprotein D Subunit Vaccines on the Development of Primary, Recurrent, and Latent Genital Infections With Herpes Simplex Virus Type 2 in Guinea Pigs. *J. Infec. Dis.,* 157(5):897–902 (May 1988); Blacklaws, B. et al., Immunogenicity of herpes simplex type 1 glycoproteins expressed in vaccinia virus recombinants. *Virology,* 177:727–736 (1990); Spear, P. G., Glycoproteins specified by herpes simplex virus. In: *The herpesviruses,* edited by Roizman, B., New York, Plenum Press, pp. 315–356 (1985); Narrild, B., Humoral response to herpes simplex virus infections. In: *The herpesviruses,* edited by Roizman, B., New York, Plenum Press, pp. 69–86 (1985); and Sarminto, M. et al., Membrane proteins specified by herpes simplex virus III. Role of glycoprotein VP7 (B2) in virion infectivity. *J. Virol.,* 29:1149–58 (1979), incorporated herein by reference); whereas patients with frequently recurring HSV have high titers of anti-HSV antibodies. Ophthalmologists have also demonstrated that patients with exuberant immune responses, such as atopes, develop the worst clinical manifestations of stromal herpetic keratitis. Whereas immunosuppressed patients, in contrast, show exacerbated epithelial keratitis but minimal stromal disease. Hence, immunotherapy capable of inducing a specific higher than normal cellular immune response is needed to combat recurrent ocular HSV infections.

Another factor attributing to recurrent ocular HSV infection is the absence of blood vessels in the cornea. Because the cornea is devoid of blood vessels, systemic immune responses have thus far been inefficient at providing protection from antigenic insults there. Stanberry, L. R. et al., Heterologous Versus Homologous Herpes Simplex Virus Glycoprotein Immunotherapy of Recurrent Genital Herpes. *Pediatr Res.,* 25:191A, Part 2 (1989). Consequently, local immunity may be particularly important in protection against ocular HSV. There is therefore a need to develop improved systemic vaccines for ocular HSV, and to develop local ocular immunotherapy to augment the immune response and control recurrent ocular HSV infection.

Currently, commercial HSV vaccine development is directed exclusively to the problem of genital HSV-2. There is minimal effort directed to combat ocular HSV-1. Yet the development of a therapeutic vaccine, that is, a vaccine to reduce HSV ocular recurrences, would greatly alleviate what is now the most frequent serious viral eye infection in the U.S. and a major cause of viral induced blindness in the world. Likewise, the development of a prophylactic vaccine to protect against infection by HSV would similarly be of tremendous importance to reducing the incidence of viral induced blindness. The present invention satisfies these needs and provides related advantages as well. The disclosures of all publications cited herein are expressly incorporated by reference.

B. DNA Technology

Recombinant DNA and associated technologies can be applied to effectively provide the large quantities of high quality bioactive HSV glycoproteins and proteins required for a therapeutic or prophylactic HSV vaccine.

DNA technology involves in part, producing a replicable expression vehicle by the DNA recombination of an origin of replication, one or more phenotypic selection characteristics, an expression promoter, a heterologous gene insert and remainder vector. The resulting expression vehicle is introduced into cells by transformation and large quantities of the recombinant vehicle obtained by growing the transformant. Where the gene is properly inserted with reference to portions which govern the transcription and translation of the encoded DNA message, the expression vehicle may produce the polypeptide sequence for which the inserted gene codes. This process of producing the polypeptide is called "expression." The resulting product may be obtained by lysing the host cell, and recovering the product by appropriate purification.

A wide range of host cells can be used, including prokaryotic and eukaryotic organisms. In addition to microorganisms, cultures of cells derived from multicellular organisms, whether vertebrate or invertebrate, may also be used as hosts.

C. Definitions

As used in this disclosure, the following terms are to be understood in relation to the following definitions.

ADJUVANT: a substance that enhances, nonspecifically, the immune response to an antigen. An adjuvant is usually administered with antigen, but may also be given before or after antigen. Adjuvants disclosed within the subject invention include but are not limited to, alum, Freund's, MTP-PE, ISCOMs, Quil A and liposomes.

ALUM: antigen absorbed into floccules of aluminum salts. Alum is the only adjuvant currently approved by the FDA for human use.

EXPRESSION VECTOR: a vehicle used to carry inserted foreign (heterologous) DNA for the purpose of producing more material or a glycoprotein or protein product. "Expression vector" includes vectors which are capable of expressing the DNA sequences it contains, where such sequences are operably linked to other sequences capable of effecting their expression. Any DNA sequence which is capable of effecting expression of a specified DNA code disposed within the sequence is included in this term as it is applied to the specified sequence. In general, expression vectors of utility in recombinant DNA techniques are often in the form of plasmids; however, this invention is intended to include other forms of expression vectors which serve equivalent functions and which subsequently become known in the art.

FREUND'S: A water-in-oil emulsion. There are two forms of Freund's adjuvant, depending on the presence or absence of killed Mycobacteria. Complete Freund's adjuvant contains *Mycobacterium tuberculosis,* or other Mycobacteria strains. Weak antigens may be rendered more immunogenic when incorporated in complete Freund's adjuvant. Incomplete Freund's adjuvant lacks Mycobacteria and is less stimulatory.

GLYCOPROTEIN: a class of compounds in which protein is combined with carbohydrate.

MTP-PE: muramyl tripeptide phosphatidyl ethanolamine, a new proprietary adjuvant developed by CIBA and refined by Chiron. It is a potent and well tolerated derivative of Freund's, and has proven to be much more effective than alum.

ISCOM (Quil A): immunostimulating complexes comprising purified proteins and the glycoside Quil A to form a honeycomb like structure that exhibits strong adjuvant activity.

IMMUNOTHERAPY: enhancement of an immune response by any one or more of a variety of adjuvants incorporating one or more antigens.

LIPOSOMES: synthetic lipid vesicles consisting of phospholipid bilayers surrounding one or more aqueous compartments. Antigens can be imbedded in the liposomes for induction of immune responses.

PLASMID: circular double stranded DNA which, in vector form, is not bound to the chromosome.

PROMOTER: a region of DNA involved in the binding of RNA polymerase to initiate transcription.

VACCINE: a composition which produces active immunity. A vaccine is comprised of materials from microorganisms that contain antigens in an innocuous form with or without one or more adjuvants. The materials may comprise antigenic determinants and/or subunits from the microorganism and may be in the form of glycoproteins or proteins.

PROPHYLACTIC VACCINE: an active immunity inducing composition given to naive individuals to prevent or ameliorate primary infection and prevent the establishment of latent infection.

THERAPEUTIC VACCINE: an active immunity inducing composition given to individuals with latent or recurrent infection to reduce or minimize recurrences.

SYSTEMIC VACCINE: a composition for inducing active immunity relating to the entire individual as distinguished from any one individual area.

LOCAL VACCINE: a composition for inducing active immunity relating to one individual area as distinguished from the entire individual.

SUMMARY OF THE INVENTION

The purpose of this invention is to produce, by recombinant DNA techniques, HSV glycoproteins or non-glycoprotein polypeptides, including but not limited to a gD-related, gB-related or Vmw65-related protein, which may be used as an immunogen in a vaccine to protect against HSV-1 and/or HSV-2 infections. Vaccines made from genetically engineered immunogens should be safer than conventional vaccines made from attenuated virus because there is no risk of infection to the recipient; and specifically with the herpes virus, there should be no risk of cervical cancer. Alternatively, the genetically engineered glycoprotein or protein product may be used to produce antibodies for use in passive immunotherapy.

Methods and compositions are therefore provided for the cloning and expression of one or more HSV glycoprotein or non-glycoprotein genes in single-cell host organisms. However, the present invention could be practiced in any cell line that is capable of the replication and expression of a compatible vector, including but not limited to, CHO and Vero cell lines. The invention is also intended to include expression vectors which serve equivalent functions as that described herein, and which become known in the art subsequently to this application. Also described are methods for culturing these novel single-cell organisms to produce the HSV gene product and methods for the purification of the gene product.

A human host is then preferably inoculated with a vaccine comprising an immunity inducing dose of one or more HSV glycoproteins or proteins of the invention, preferably a mixture of four, five, six, or seven glycoproteins, more preferably a mixture of five, six, or seven glycoproteins, more preferably still, a mixture of six or seven glycoproteins, and most preferably a mixture of seven HSV glycoproteins, wherein said glycoprotein mixture includes gB and gD, more preferably said mixture includes gB, gD, gC, gE, and gI. The vaccine can be administered by the systemic route, the enteric route, or by the ocular route. When administered by the ocular route, the vaccine can be given alone or in combination with systemic and/or enteric vaccination. The vaccine may also comprise one or more adjuvants administered with, before or after the glycoprotein component of the vaccine. Typically, one or several inoculations of between about 10–1000 μg each are sufficient to effect immunization of a human host.

The vaccine of the invention may be conveniently utilized in liquid form, freeze-dried, spray dried or lyophilized form, in combination with one or more suitable preservatives and protective agents to protect the glycoproteins or proteins during processing.

A. Antigens

The HSV-1 glycoproteins comprising the subject immunotherapy include but are not limited to glycoproteins gB, gC, gD, gE, gG, gH, gK, gL, gI, Vmw65, ICP0 and ICP4. The HSV-1 glycoproteins may be native, purified native, recombinant and/or synthetic. The recombinant glycoproteins may be obtained by the procedure set forth below, or any equivalent procedure. The vaccine may comprise one or more of these glycoproteins in a dose of 10–1000 μg per inoculation.

B. Adjuvants

Vaccines are often administered in an emulsion with various adjuvants. The adjuvants aid in attaining a more durable and higher level of immunity using smaller amounts of antigen in fewer doses than if the immunogen were administered alone. The adjuvants for use in the present invention include but are not limited to alum, Freund's, MTP-PE and ISCOMs (Quil A). In addition, the vaccine may comprise a liposome or other membrane bound vesicle comprising one or more HSV-1 glycoproteins administered with or without one or more adjuvants to induce the cell mediated immune response.

C. Immunization Routes

The ocular route is the preferred route of inoculation; however, this designation as the preferred inoculation route is not meant to preclude any other route of administration. For example, when combinations of glycoproteins are used in a mixture, particularly where the mixture comprises at least five glycoproteins which include gB and gD, systemic administration is similarly effective. The vaccine can be administered by the ocular route either alone or in combination with systemic (intramuscular or subcutaneous) and enteric vaccination. The ocular route includes but is not limited to subconjunctval injection, surface drops, a slow-release device such as a collagen shield, a hydrogel contact lens or an ALZA "Ocusert."

Subconjunctival vaccination is done using proparacaine for anesthesia prior to the injection of 0.2–0.5 ml of vaccine, in a dose of 10–1000 μg/inoculation, given in an insulin syringe and a small gauge needle. The injection is given in the lower cul-de-sac ensuring that the vaccine material remains subconjunctival and does not leak out.

The surface drops vaccination involves placing 50 μl of expressed glycoproteins with or without adjuvant in the conjunctival cul-de-sac and then rubbing the eye gently for 30 seconds while held closed. Since the expressed glycoprotein may be quickly cleared, the procedure should be repeated four times a day for five days to prolong the exposure, all of which comprise a single vaccination. For better retention, the tear drainage ducts may be temporarily blocked using collagen or other devices.

A collagen shield may also be soaked in a concentrated solution containing glycoproteins and adjuvant and then placed in the eye like a contact lens. The lid is then closed for several days by external application of medical grade cyanoacrylate adhesive, during which time the antigen is continuously released. Alternatively, the glycoproteins may be encapsulated in a microcapsule and then implanted into the eye to facilitate continuous antigen release.

C. Expression System For The Glycoproteins

Consistent high expression of the HSV-1 glycoproteins from the same source is an important factor in the development of a human HSV vaccine. Until recently, studies have been hampered by the diverse expression vectors and the diverse viral sources of the various HSV-1 glycoproteins expressed, making meaningful comparison among the expressed glycoproteins difficult. To overcome this problem, we have individually expressed high levels of seven HSV-1 glycoproteins from one virus strain in a single vector system as outlined in detail in Section V below.

The examples set forth below describe use of baculovirus, the polyhedron promoter system and insect cells as host cells. However, it would be well within the skill of the art to use analogous techniques to construct expression vectors for expression of desired glycoprotein and protein products in alternative host cell cultures.

D. Test Model

An important tool in the development of a human ocular HSV vaccine is the test animal model used. Our test system for ocular vaccine administration is the rabbit eye because HSV infections there very closely simulate what happens in the human eye. For instance, the severity of the eye disease is similar, latency is similarly established, and spontaneous reactivations occur much as they do in humans. Alternatively, for systemic vaccine administration, our test system is the mouse, preferably BALB/C mice.

The invention relates generally to immunotherapy for the treatment of HSV infection in a human host. The invention also relates to the expression of high levels of high quality bioactive HSV-1 glycoproteins or proteins from one virus strain in a single vector system.

One aspect of the invention involves a systemic vaccine comprising one or more HSV-1 glycoproteins or proteins to decrease spontaneous HSV-1 shedding and to reduce the incidence of primary HSV-1 infection. Another aspect of the invention involves a local ocular therapeutic vaccine comprising one or more HSV-1 glycoproteins or proteins to decrease spontaneous HSV-1 ocular shedding and thereby control recurrent corneal disease. Another aspect of the invention involves a local ocular prophylactic vaccine comprising one or more HSV-1 glycoproteins or proteins to reduce the incidence of primary HSV-1 infection.

It is therefore a general object of the present invention to develop effective immunotherapy for the treatment of HSV in a host.

It is an object of the present invention to develop effective systemic immunotherapy for the treatment or prevention of HSV in a human host.

It is an object of the present invention to develop effective local immunotherapy for the treatment of ocular HSV in a human host.

It is also an object of the present invention to develop a local therapeutic ocular vaccine to decrease spontaneous HSV ocular shedding and to control recurrent disease in a human host.

It is a further object of the present invention to develop a local prophylactic ocular vaccine to reduce the incidence of primary HSV infection in a human host.

It is still further an object of the invention to utilize an animal test model that closely simulates HSV infection in the human eye.

It is another object of the present invention to individually express high levels of the seven HSV-1 glycoproteins from one virus strain in a single vector system.

These and other objects will become readily apparent to those skilled in the art from the following description and appended claims.

BRIEF DESCRIPTION OF THE DRAWINGS

The present invention will be described in connection with the accompanying drawings in which.

DETAILED DESCRIPTION OF THE INVENTION

Figure 1:
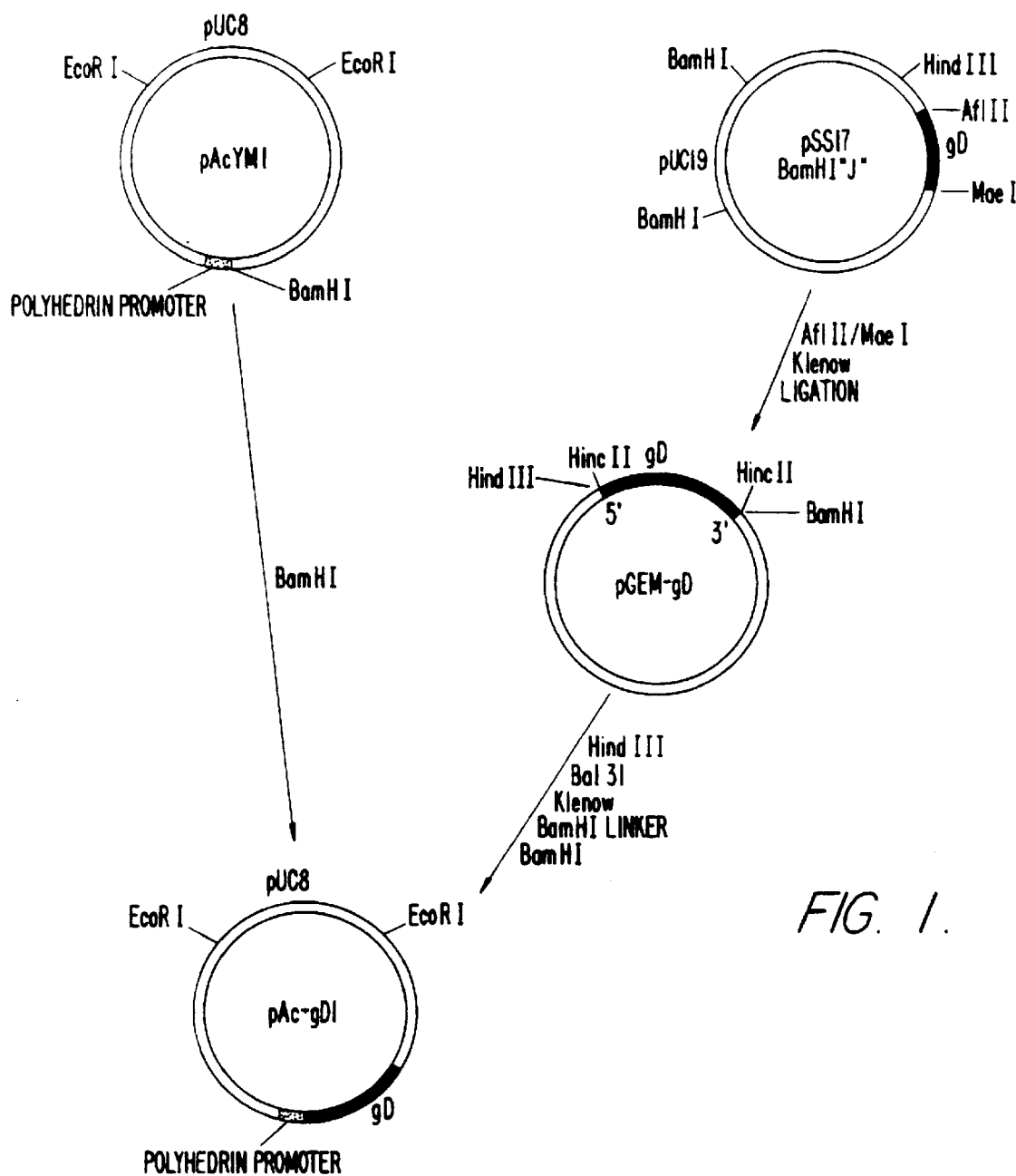
FIG. 1 is a schematic diagram of the construction of plasmid pAC-gD1 used in constructing exemplary recombinant virus strains of the invention.

The present invention utilizes recombinant DNA techniques to insert a DNA sequence coding for an HSV-1 glycoprotein, protein, or a portion thereof, into a DNA vector, such that the vector is capable of replicating and directing expression of the glycoprotein or protein gene in a foreign host. The resulting recombinant DNA molecule is introduced into insect cells to enable high production of the glycoprotein, or protein, or a portion or molecular variant thereof by the host cells. The glycoprotein or protein produced is then isolated and purified for use in immunotherapy against both HSV type 1 and type 2.

A. Preparation Of HSV-1 Glycoproteins

It is to be understood that other procedures may be utilized and that changes may be made without departing from the scope of the invention. The following detailed description is, therefore, not to be taken in a limiting sense, and the scope of the present invention is best defined by the appended claims.

1. Baculovirus expression of HSV-1 gD

The DNA sequence encoding the complete herpes simplex virus type 1 (HSV-1n) glycoprotein D (gD) was inserted into a baculovirus transfer vector under control of the polyhedron gene promoter of the baculovirus *Autographa californica* nuclear polyhedrosis virus (*Ac*NPV). After co-transfection of *Spodoptera frugiperda* (*Sf*9) insect cells with wild-type *Ac*NPV DNA and the recombinant transfer vector DNA, polyhedron-negative recombinants that expressed high levels of HSV-1 gD were isolated using immunoaffinity selection with antibody coated magnetic particles followed by plaque purification. These recombinant baculoviruses expressed a protein that was slightly smaller than virion HSV-1 gD made in Vero cells. The HSV-1 gD recombinant protein was expressed at high levels, was glycosylated, was found on the membrane of *Sf*9 cells, and reacted with gD specific antibodies. The procedure is described in detail (Ghiasi et al., Arch. Virol. 121:163–178 (1991), incorporated herein by reference) as follows:

a. Materials and methods i. Viruses and cells

The E2 strain of *Autographa californica* nuclear polyhedrosis virus (*Ac*NPV) (baculovirus) and *Spodoptera frugiperda* clone 9 (*Sf*9) insect cells were gifts from Dr. Max Summers, Texas A & M. Insect cells were grown in TNM-FH media containing 10% fetal bovine serum. Summers, M. D., Smith, G. E., *A manual of methods for baculovirus vectors and insect cell culture procedures.* Micro Gene Sys., New Haven (1988). Wild-type and recombinant baculoviruses were grown according to the procedures of Summers and Smith. Summers, M. D., Smith, G. E., *A manual of methods for baculovirus vectors and insect cell culture procedures.* Micro Gene Sys., New Haven (1988). Plaque purified HSV-1 (strains McKrae and KOS) and Vero cells were grown using standard techniques as previously described. Rock, D. L., Nesburn, A. B. et al., Detection of latency related viral RNAs in trigeminal ganglia of rabbits latently infected with herpes simplex virus type 1. *J. Virol.,* 61:3820–26 (1987).

ii. Construction of *Ac*NPV recombinant transfer vector

Plasmid pSS17 (HSV-1 strain KOS, a gift from D. C. Johnson, Ontario, Canada), or alternatively plasmid pSG25, both of which are available by procedures well known in the art (see Neidhardt et aol., J. of Virology 61(2):600–603 (1987); Hanke et al., Virology 177:437–444 (1990); Johnson et al., J. of Virology 62(4):1347–1354 (1988); and Goldin et al., J. of Virology 38(1):50–58 (1981), incorporated herein by reference) was double digested with Afl II/Mae I and the 1.2 kb fragment containing the complete coding region of gD was isolated and blunt ended into the Hinc II site of pGEM3 (see FIG. 1). The construct was linearized with Hind III, digested briefly with Bal 31 exonuclease to remove unwanted nucleotides upstream from the first ATG in the coding sequence, and BamHI linker was added. The resulting fragment was isolated and ligated into the unique BamHI site of the vector pAcYM1 in lieu of the polyhedron structural gene (under control of the strong polyhedron gene promoter) (Matsuura, Y. et al., Baculovirus expression vectors: the requirements for high level expression of proteins, including glycoproteins. *J. Gen. Virol.,* 68:1233–50 (1987), incorporated herein by reference), or into a like plasmid adapted for similar use, such as pBacPAK8, pBacPAK9, and pAcUW31 commercially available from Clontech (Palo Alto, Calif.) and pAcUW41, pAcUW51, and pAcUW21 commercially available from Pharmingen (San Diego, Calif.). Partial sequence analysis indicated that the cloned gD has a short noncoding region of 6 nucleotides at the 5' end. No HSV noncoding sequences are present after the termination codon (TAG) at the 3' end.

iii. Preparation of magnetic particles for selection of recombinant gD

Ten ml of magnetic goat-anti rabbit IgG (Advanced Magnetics Inc., Cambridge, Mass.) were transferred to a 75 ml tissue culture flask. A large magnet (supplied by the manufacturer) was placed on one flat surface of the flask to attract and retain the magnetic goat anti-rabbit IgG and the supernatant was decanted and discarded. After washing the magnetic material with coupling buffer (100 mM PBS pH 7.4, 0.1% BSA, 0.1% non-fat dry milk, and 1 mg/ml *Ac*NPV total protein extract) 1 ml of gD polyclonal antibody (40 $\mu$g) in 9 ml coupling buffer was added to the BioMag (magnetic goat anti-rabbit IgG). The mixture was agitated overnight at 4° C., and then magnetically separated. After two successive washes with coupling buffer and two washes with TNM-FH, the BioMag-gD antibody complexes were resuspended in 10 ml TNM-FH and stored at 4° C.

iv. Transfection and selection of recombinant viruses

*Sf*9 cells were cotransfected with purified infectious *Ac*NPV DNA and pAc-gD 1 plasmid DNA essentially as described. Summers, M. D., Smith, G. E., *A manual of methods for baculovirus vectors and insect cell culture procedures.* Micro Gene Sys., New Haven (1988). After four days of incubation at 28° C. and the appearance of CPE, the infected cells were screened by immunoaffinity selection. The cell pellet was harvested and incubated with 1 ml of anti-gD antibody-coated magnetic particles and 1 ml of media for 60 minutes on ice. The cell suspension was magnetically separated, fresh media was added to the magnetically collected cells and separation (washing) was repeated five times at room temperature. The selected material was used to infect confluent monolayers of *Sf*9 cells. Following viral growth the supernatant was titrated on confluent monolayers of *Sf*9 cells. Plaques exhibiting no evidence of occlusion bodies (viral polyhedra) as determined by transmission light microscopy were recovered and retitered on *Sf*9 cells to obtain recombinant, polyhedron-negative viruses. Following a third plaque picking, high titered stocks ($10^7$–$10^8$ PFU/ml) of recombinant viruses were obtained.

V. Preparation of viral DNA

*Sf*9 cells were infected with recombinant virus at a multiplicity of 10 PFU/cell and incubated at 28° C. for 27 hours. The infected cells were freeze-thawed and centrifuged for 10 minutes at 1000×g to remove cell debris. The procedures used for virus isolation and viral DNA extraction (from the supernatant fluid) and blotting have been previously described (Inumaru, S. et al., Expression of bluetongue virus group specific antigen VP3 in insect cells by a baculovirus vector: its use for the detection of bluetongue virus antibodies. *J. Gen. Virol.* 68:1627–35 (1987), incorporated herein by reference).

vi. Western blots

Western immunoblot analyses were carried out under denaturing conditions. Samples for SDS-PAGE were disrupted in electrophoresis sample buffer containing 2% SDS and 10% 2-mercaptoethanol and heated at 100° C. for three minutes. Proteins were separated by SDS-PAGE (Laemmli, U. K., Cleavage of structural proteins during the assembly of the head of bacteriophage T4. *Nature,* 227:680–85 (1970), incorporated herein by reference), and transferred to nitrocellulose paper by electrophoresis as described by Towbin et al. (Towbin, H. T. et al., Electrophoretic transfer of proteins from polyacrylamide gels to nitrocellulose sheets: procedures and some applications. *Proc. Natl. Acad. Sci.,* 76:4350–54 (1979), incorporated herein by reference). After transfer, nitrocellulose blots were blocked in BLOTTO (5% nonfat dry milk in PBS) and then reacted with anti-gD polyclonal antibody or total HSV-1 antibody 1 hour at 4° C. Bound antibody was detected by reacting the blots with $^{125}$I-protein A for 1 hour at 25° C. followed by autoradiography.

vii. Endoglycosidase H and endoglycosidase F

To determine if complex sugars were added as part of the gD glycosylation protein, Endoglycosidase H (Endo-H) and Endoglycosidase F (Endo-F) treatments were done on lysed infected cells as described by the manufacturer (Boehringer Mannheim Biochemicals). Endo-H removes high mannose chains while Endo-F removes both high mannose and hybrid sugars.

viii. Tunicamycin treatment

To determine if the expressed gD underwent N-glycosylation, infected cell monolayers were treated with 4 µg/ml tunicamycin (an inhibitor of asparagine-linked glycosylation) in TNM-FH media for 48 hours as described (Jarvis, D. L., Summers, M. D., Glycosylation and secretion of human tissue plasminogen activator in recombinant baculovirus infected insect cells. *Mol. Cell. Biol.,* 9:214–23 (1989), incorporated herein by reference).

ix. Immunofluorescence

*Sf*9 cells were infected with wild-type *Ac*NPV or recombinant baculoviruses expressing gD at a multiplicity of infection of 10 PFU/cell and incubated for 72 hours. To look at total fluorescence, cells were washed with PBS, fixed with acetone and anti-gD polyclonal antibody (provided by Dr. Richard Eberle) was added and incubated for 1 hour at 37° C. Alternatively, to determine cell surface immunofluorescence, unfixed, unpermeabilized cells were washed with PBS and incubated with antibody for 1 hour at 4° C. After washing, slides were fixed with acetone. Slides for total and surface fluorescence were then washed with PBS, stained with fluorescein-conjugated goat anti-rabbit IgG antibody for 1 hour at 37° C., washed again with PBS, and examined for fluorescence.

2. Results a. Construction of recombinant viruses expressing gD

The strategy for the construction of the baculovirus transfer vector containing the complete gD open reading frame from HSV-1 is shown in FIG. 1. A complete DNA copy of the gD gene from the BamHI J fragment, was isolated by restriction enzyme digestion with AflII/MaeI. Most of the 5' noncoding sequences were removed by Bal31 digestion. The resulting DNA was then inserted into the BamHI site of the pAcYM1 vector (FIG. 1). As confirmed by restriction enzyme analysis and partial sequencing, this construct contains the entire sequence of the gD gene. It has a non-coding region of only 6 nucleotides in front of the first ATG. This is followed by the complete coding region of 1182 nucleotides. To transfer the gD gene into the baculovirus *Ac*NPV genome, *Sf*9 cells were cotransfected with pAc-gD1 DNA and infectious *Ac*NPV DNA. Putative recombinant viruses were enriched by immunoaffinity selection, which was followed by three cycles of polyhedron-negative plaque purification. In this study, one round of immunoselection increased the efficiency of obtaining recombinant viruses by several fold with yields of better than 8% recombinants in the first plaque purification cycle.

b. Western blot analysis

Figure 2:
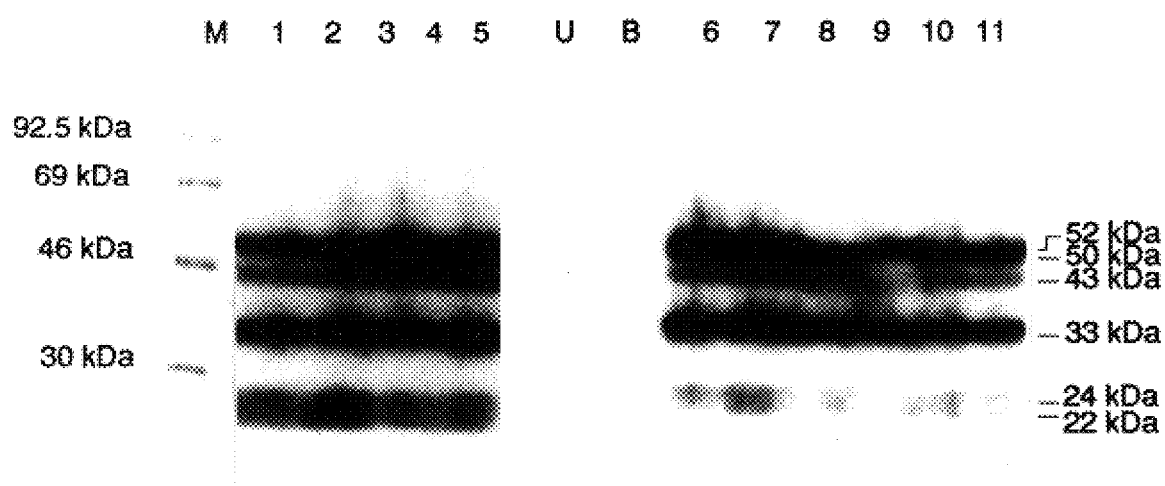
FIG. 2 is a Western Blot analysis of eleven recombinant baculoviruses expressing HSV-1 glycoprotein in insect cells. Lane M represents molecular weight markers.
Figure 5:
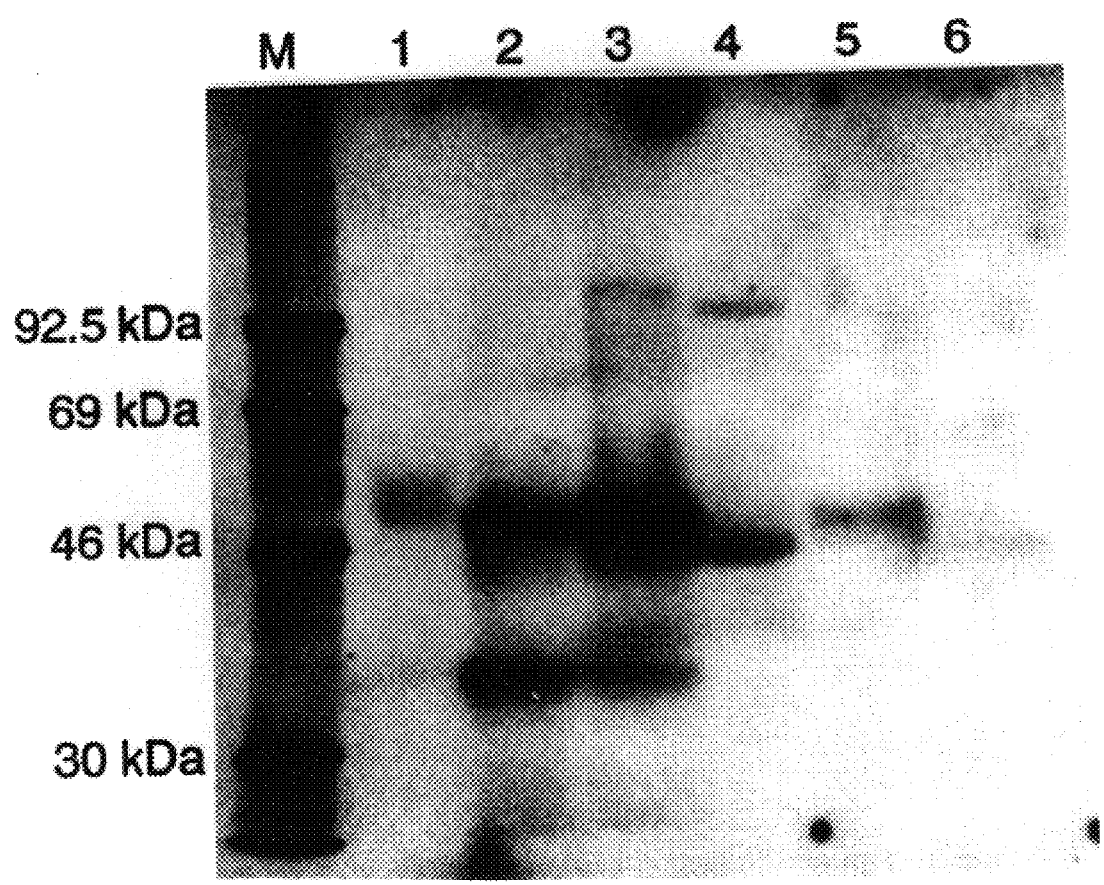
FIG. 5 is a Western Blot analysis of baculovirus expressed gD glycosylation. M. molecular weight markers; 1. Vero cells infected with HSV-1 at an MOI of 10 for 24 hr.; 2. vAc-gD1 infected cells at 48 hr.; 3. vAc-gD1 infected cells at 72 hr.; 4. Tunicamycin treated vAc-gD1 infected cells; 5. Endo-H treated vAc-gD1 infected cells; 6. Endo-F treated vAc-gD1 infected cells.

Confluent monolayers of *Sf*9 cells were infected at a multiplicity of 10 PFU/cell with 11 individual recombinant baculoviruses obtained after three plaque purifications and total protein extracts were analyzed by Western blotting. Our vAc-gD1 recombinants produced 6 protein bands that reacted with both total HSV-1 polyclonal antibody (FIG. 2) and gD polyclonal antibody (FIG. 5). A band with an apparent molecular weight of 43 kDa corresponds to the non-glycosylated primary gD polypeptide that has a predicted molecular weight of 43,291 Da. Two larger bands (50 kDa and 52 kDa) ran as a very tight doublet that was not resolved in this blot. These two bands presumably represent the partially glycosylated precursor pgD and mature gD (Lee, G. T. et al., Location of the structural genes for glycoproteins gD and gE and for other polypeptides in the S component of herpes simplex virus type 1 DNA. *J. Virol.,* 43:41–49 (1982); and Mathews, J. T. et al., Synthesis and processing glycoprotein D of herpes simplex virus types 1 and 2 in an in vitro system. *J. Virol.,* 48:521–53 (1983), incorporated herein by reference) respectively.

The three smallest bands had apparent molecular weights of 33, 24, and 22 kDa. A similar pattern of bands was obtained with immunoaffinity column (Affi-Gel 10; Bio-Rad) purified gD (using gD monoclonal antibody, a gift from Dr. D. Wiley).

Western blot analysis of recombinant infected cell medium did not detect any gD. This suggests that the expressed gD is retained in the cell or in the cell membrane as with HSV-1 infected cells and is not secreted into the medium.

c. Southern blot analysis

Figure 3A:
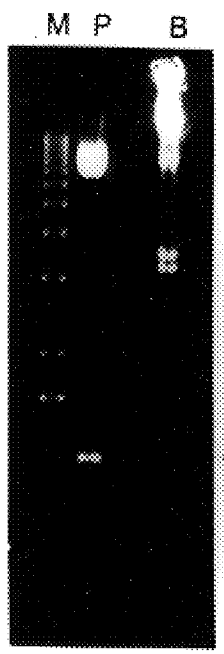
FIG. 3 is a Southern Blot analysis of recombinant baculovirus DNA; a. Ethidium bromide staining gel; b. Autoradiogram; M. markers (IKb); P. plasmid-BamHI cut pAc-gD1 transfer vector; B. baculovirus recombinant BamHI cut DNA. Arrows indicate the location of the BamHI released gD structural gene from the initial vector (pAc-gD1) and from the recombinant baculovirus (vAc-gD1).
Figure 3B:
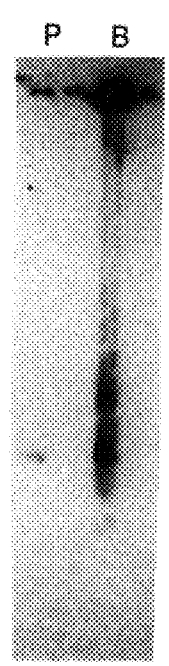

Since no obvious differences in the expression levels or the sizes of any of the gD related bands were seen among the 11 recombinant viruses, one recombinant virus was arbitrarily selected for subsequent study and designated vAc-gD1. To verify the presence of full length HSV-1 gD DNA in vAc-gD1, the baculovirus DNA was digested with the restriction enzyme BamHI and Southern blots were done using the gD gene as a probe (FIG. 3). As can be seen by both ethidium bromide staining of the DNA (FIG. 3a) and Southern analysis using a gD specific probe (FIG. 3b), BamHI digestion of the gD recombinant generated a band of the expected size (approximately 1.2 kb). This corresponds to the HSV-1 gD gene cloned into the expression vector (FIG. 3).

d. Visualization of expressed gD by SDS-PAGE and coomassie blue staining

Figure 4:
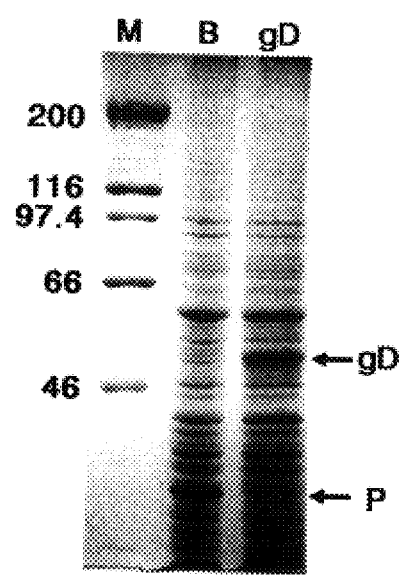
FIG. 4 is a commassie blue staining of recombinant baculovirus infected cell extracts following SDS-PAGE. M. molecular weight markers; B. wild type baculovirus infected cells; gD.vAc-gD1. The arrows on the right indicate the positions of the major glycosylated gD band in gD and the wild type polyhedron protein visible in B.

Total cell extracts from wild type baculovirus and vAc-gD1 recombinant baculovirus infected cells were run on SDS-PAGE and protein bands were stained with coomassie blue. The polyhedron protein band seen in wild type baculovirus infected cells (FIG. 4, lane B) was missing in vAc-gD1 infected cells, while a new, larger band of similar intensity was present in the vAc-gD1 infected cells (FIG. 4, lane gD). Neither band was seen in uninfected cells. This new recombinant band had an apparent molecular weight of approximately 50–52 kDa, corresponding in size to the tight doublet upper bands seen by Western analysis (FIG. 2, bands 50 and 52 kDa), and represented the major expressed gD species in this recombinant baculovirus.

Visual observation of the stained gel suggested that the amount of expressed gD was similar to the amount of polyhedron in wild type baculovirus infected cells (FIG. 4, compare gD to P in lanes gD and B). To confirm this and to more accurately estimate the relative expression level of gD, the coomassie blue stained gel shown in FIG. 4 was scanned on a laser densitometer. The area under the combined peak representing gD and pgD was similar to the area under the peak for the polyhedron protein in wild type baculovirus infected cells. Identical results were obtained in scans of additional gels. Since the polyhedron protein has been estimated to comprise up to 40% of total cellular protein, this analysis indicates that the recombinant gD is expressed at very high levels (Takedara, K. et al., Co-expression of the Hepatitis B surface and core antigens using baculovirus multiple expression vectors. *J. Gen. Virol.,* 69:2763–777 (1988), incorporated herein by reference).

e. Glycosylation of gD

To confirm that the expressed gD underwent glycosylation, tunicamycin treatment was done to prevent N-glycosylation in infected Sf9 cells. Infected cells were treated with 4 μg tunicamycin/ml of TNM-FH media from 0–48 h post infection, and total cell extracts were analyzed by Western blots using polyclonal anti-gD antibody. The tunicamycin treatment (FIG. 5, lane 4n) reduced the apparent size of gD relative to the control (lanes 2 and 3). This result indicates that like native gD, the untreated expressed gD was glycosylated and contained N-linked sugars.

To determine if the expressed gD contained complex sugars, vAc-gD1 infected cell lysates were treated with Endoglycosidase-H (Endo-H, removes high mannose sugars) or Endoglycosidase-F (Endo-F, removes high mannose and hybrid sugars). As seen in FIG. lane 5, gD was partially resistant to digestion by Endo-H. In contrast, Endo-F digestion decreased the apparent molecular weight of gD to approximately 45 kDa (FIG. 5, lane 6). Thus, similar to native gD, the expressed gD was partially resistant to Endo-H and susceptible to Endo-F. Therefore, like native gD the recombinant gD was glycosylated and contained N-linked hybrid sugars.

f. Immunofluorescence of recombinant gD in insect cells

Figure 6A:
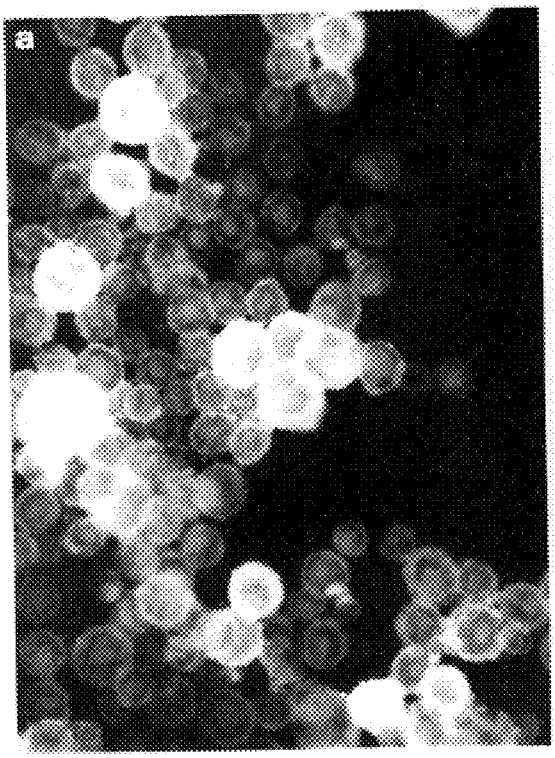
FIG. 6 shows the immunofluorescence of recombinant baculovirus-infected cells. a. Recombinant vAc-gD1 infected cells, total fluorescence; b. vAc-gD1 infected cells, surface fluorescence; c. wild type baculovirus infected cells, total fluorescence.
Figure 6B:
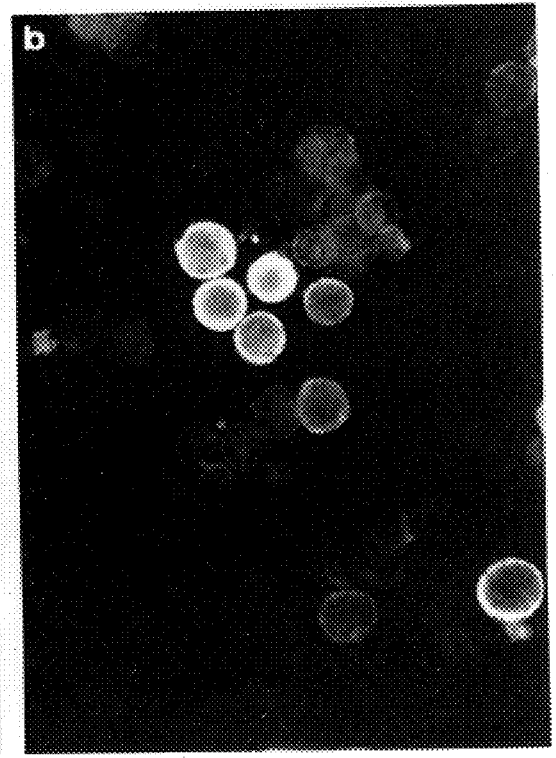
Figure 6C:

To determine whether the expressed gD was transported to the cell surface, vAc-gD1 infected Sf9 cells were examined by indirect immunofluorescent antibody staining using polyclonal antibody to gD. Immunofluorescence was readily observed in recombinant-infected cells (FIG. 6a). No immunofluorescence was seen in cells infected with AcNPV (FIG. 6c) or in uninfected Sf9 cells. To look specifically for gD on the cell surface, indirect immunofluorescent antibody staining was done on cells prior to fixation (and permeabilization) (FIG. 6b). The surface fluorescence on vAc-gD1 infected cells was strong and comparable to that observed for permeabilized fixed cells. This indicates that the expressed gD was correctly transported to and anchored in the cell surface.

3. Baculovirus expression of HSV-1 gB, gC, gD, gE gG gH or gI

Glycoproteins gB, gC, gD, gE, gG, gH and gI were similarly expressed in baculovirus (Ghiasi, H. et al., Expression of glycoprotein B of herpes simplex virus type 1 in insect cells: analysis of its biochemical and immunological properties. *Virus Res.,* 22:25–39 (1991); Ghiasi, H., et al., Baculovirus expressed herpes simplex virus type 1 glycoprotein C protects mice from lethal HSV-1 infection. *Antiviral Research,* 18:291–302 (1992); Ghiasi, H., et al., Baculovirus expressed glycoprotein E (gE) of herpes simplex virus type 1 (HSV-1) protects mice against lethal intraperitoneal and lethal ocular HSV-1 challenge. *Virol.* 188:469–476 (1992); Ghiasi, H., et al., Synthesis and immunogenicity of glycoprotein G (gG) of herpes simplex virus type 1 expressed by recombinant baculoviruses. *Virol.* 190:233–239 (1992); Ghiasi, H., et al., Cell surface expression of herpes simplex virus type 1 glycoprotein H in recombinant baculovirus infected cells. *Virology,* 185:187–194 (1991); Ghiasi, H., et al., Expression of the herpes simplex virus type 1 (HSV-1) of glycoprotein I (gI) in baculovirus: Preliminary biochemical characterization and protection studies. *J. Virol.,* 66:2505–2509 (1992); and McGeoch et al., *J. of Gen. Virol.* 69:1531–1574 (1988), incorporated herein by reference.) In all cases, high level expression of a protein similar in size to the native glycoprotein was obtained. All the expressed glycoproteins were glycosylated, reacted with the appropriate monoclonal or polyclonal antisera, and were correctly transported to the cell surface.

B. Vaccination

1. Outline of Vaccine Trial

Rabbits. New Zealand White (NZW) male rabbits (approximately 2 kg each) are used for all experiments. As discussed above, these animals develop a primary and recurrent ocular herpetic disease that mimics HSV keratitis in man.

Virus and vaccines. McKrae, a highly pathogenic stromal disease causing HSV-1 strain, with a very high spontaneous reactivation rate is used for establishment of latency. Strain RE or W will be used in some experiments to confirm that results are not strain specific.

Day 0: Ocular infection for establishment of latency. Rabbits are bilaterally infected by placing $2 \times 10^5$ PFU (McKrae) into the conjunctival cul-de-sac, closing the eye, and rubbing gently for 30 seconds. Although this dose of virus results in the death of approximately 30% of the rabbits, this is the lowest dose at which all survivors become latently infected in both eyes (really both trigeminal ganglia). Although latency cannot be judged at this point without the loss of the rabbit for the vaccine experiment, our extensive experience indicates that virtually every trigeminal ganglia harbors HSV-1 latency under these conditions. At the termination of the vaccine trial, the trigeminal ganglia from those eyes that have not shown spontaneous or induced reactivation will be removed and explant co-cultivation done to confirm that latency had been established. In our experience this strain and dose combination results in the highest number of known latently infected and spontaneously reactivating eyes, (starting with a given number of rabbits) thus using the fewest possible rabbits. Also with this regimen, no more than 1% of rabbits become blind in both eyes (these rabbits are immediately sacrificed).

Subconjunctival vaccination is done using topical proparacaine for anesthesia prior to subconjunctival injection of 0.2–0.5 ml of vaccine given with an insulin syringe and a small gauge needle. The injection is given in either the upper or lower cul de sac making an effort that the vaccine material remains subconjunctival and does not leak out.

Enteric vaccination is done by gavage down the rabbits throat.

Vaccination by surface drops and collagen shield is as described above.

Glycoprotein purification. Glycoproteins will be purified by differential centrifugation of freeze-thawed or detergent disrupted cell extracts, followed by immunoaffinity purification through columns with covalently bound HSV-1 antibody.

ISCOMs with Quil-A are made as previously described in the literature (Morein, B. et al., Iscom, a novel structure for antigenic presentation of membrane proteins from enveloped viruses. *Nature,* 308:457–60 (1984); and Goldstein, D. J., Weller, S. K., Factor(s) present in herpes simplex virus type 1 infected cells can compensate for the loss of the large subunit of the viral ribonucleotide reductase: characterization of an ICP6 deletion mutant. *Virology,* 166:41–51 (1988), incorporated herein by reference).

Day 21: Latency is considered to be established in all survivors (see Specific methods below for a discussion).

Rabbits are randomly divided into trial and control groups and vaccinated ocularly.

Day 35: Vaccination repeated.

Day 49–118: Tear films are collected once a day, 5 days a week to look for spontaneous shedding indicative of HSV reactivation.

Day 49–118: Eyes are examined 3×/week (prior to tear film cultures) by slit lamp biomicroscopy to directly monitor epithelial keratitis, stromal disease and scarring.

Ocular parameters. Severity of ocular disease is scored on a 0 to 4 scale in a masked fashion by examination with slit lamp biomicroscopy using 1% methylene blue to delineate epithelial ulceration. Iritis and stromal keratitis are also scored on a 0 to 4 scale.

In vivo reactivation is done by iontophoresis with 6-hydroxydopamine followed by topical epinephrine (Shimormura, Y. et al., Shedding by iontophoresis of 6-hydroxdopamine followed by topical epinephrine. *Invest. Ophthalmol.*, 24:1588–90 (1983), incorporated herein by reference).

Blood and tear samples are taken for immunological analysis prior to initial infection (day 1), prior to vaccinations (days 20 and 34), 2 weeks after the second vaccination (day 49), and at the end of the experiment (>day 118).

In vivo reactivation. Co-cultivation of trigeminal ganglia is done as previously described (Nesburn, A. B. et al., Isolation of herpes simplex virus: Isolation from rabbit trigeminal ganglia between episodes of recurrent ocular infection. *Arch. Ophthalmol.*, 88:412–17 (1972), incorporated herein by reference).

Serum neutralizing antibody titers are done by plaque reduction assays (Nesburn, A. B. et al., Ocular safety and efficacy of an HSV-1 gD vaccine during primary and latent infection. *Invest. Ophthalmol. Vis. Sci.*, 31:77–82 (1990), incorporated herein by reference).

Local ocular sIgA and IgG titers are done using tears collected on a "sno strip" (Ashley, R., Personal communication (1990)) for human sIgA cervical HSV-2, with adjustments made to detect rabbit (rather than human) HSV-1 (rather than HSV-2) specific sIgA and IgG. Correlations between IgG and IgA neutralization titers and ELISAs will be done.

Systemic IgA and IgG titers are done from sera by ELISA (Pass, R. F. et al., Identification of Patients With Increased Risk of Infection with Herpes Simplex Virus After Renal Transplantation. *J. Infec. Dis.*, 140(4):487–492 (1979), incorporated herein by reference).

Lymphocyte proliferation responses will be monitored by checking for T cells that will proliferate upon stimulation with HSV proteins (Borenstein, L. A. et al., Immunization of rabbits with recombinant treponema palladium surface antigen 4D alters the course of experimental syphilis. *J. Immunol.*, 140:2415–21 (1988), incorporated herein by reference). Peripheral blood mononuclear cells (PBMC) are collected from latently infected, latently infected immunized, and control rabbits by venipuncture into preservative-free heparinized syringes, with subsequent purification by Ficoll-hypaque centrifugation. PBMC are resuspended to a concentration of $2.5 \times 10^5$ cells/ml in RPMI-1640 medium containing 15% heat-inactivated fetal bovine serum and antibiotics (RPMI-15% FBS). 200 $\mu$l of PBMC ($5 \times 10^4$) is added to each of four replicate round bottom microtiter plate wells, followed by the addition of 100 $\mu$l of 1.0 or 5.0 $\mu$g/ml solutions of expressed HSV-1 glycoprotein, 100 $\mu$l of UV-light inactivated HSV-1 ($10^6$ PFU/ml prior to UV irradiation), or 100 $\mu$l of RPMI-15% PBS as a control. Seven days after the onset of stimulation, 1 $\mu$Ci of [$^3$H] thymidine ([$^3$H]TdR, NEN, Boston, Mass.) is added for the last 6 hours of incubation at 37° C. Cells are then harvested by using a multiple well harvesting device, and [$^3$H]TdR incorporation determined by liquid scintillation counting.

Therapeutic effectiveness is determined by comparing ocular shedding, recurrent epithelial keratitis, recurrent stromal keratitis, and scarring to mock vaccinated controls. All animal work and analyses will be masked to eliminate bias.

2. Controls

All vaccine trials were compared to a mock vaccine for the amount of ocular shedding, the amount of recurrent stromal disease and the levels of immune response.

3. Spontaneous Ocular Shedding as a Valid Predictor of Corneal Lesions

Corneal epithelial lesions and stromal scarring are usually preceded by detectable levels of ocular HSV shedding. Hence, shedding is almost certainly a prerequisite for recurrent epithelial and stromal lesions. All else being equal, it was surmised that a decrease in shedding, i.e., less culture-detectable infectious virus in tears, will result in decreased corneal disease. Ocular shedding was therefore determined by collecting tear films once a day, five days per week from each eye and culturing them for infectious virus between day 49 (two weeks after the final vaccination) and day 118.

4. Induced Ocular Shedding

Induced ocular shedding can be accomplished by iontophoresis with 6-hydroxydopamine followed by topical epinephrine as described previously in the literature.

5. Selection of Vaccines

At present, there are ten known antigenically distinct glycoproteins in HSV-1 virions: gB, gC, gD, gE, gG, gI, gH, gK, gL, and gM (Little et al., Virology 115:149–160 (1981); Cohen et al., J. Virol. 36:429–439 (1980); Lee et al., J. Virol. 43:41–49 (1982); Longnecker et al., Proc. Natl. Acad. Sci. 84:4303–4307 (1987); Frame et al., J. Gen. Virol. 67:745–751 (1986); Buckmaster et al., Virology 139:408–413 (1984); Hutchinson et al., J. Virol. 66:5603–5609 (1992); McGeoch et al., J. Gen. Virol. 69:1531–1574 (1988); and Baines et al., J. Virol. 67:1441–1452 (1993), all of which are incorporated herein by reference). These glycoproteins are the major targets for vaccine development against HSV-1 infection (Norrild, Humoral response to herpes simplex virus infections. In: Roizman and Lopez eds. The herpesviruses. New York: Plenum Press; 1985:69–86, incorporated herein by reference). However, most HSV vaccine studies have focused on gD and gB, and gD has received the greatest attention as a subunit vaccine candidate (Long et al., Infect. Immun. 37:761–764 (1984); Cantin et al., Proc. Natl. Acad. Sci. 84:590–5912 (1987); Dix, Prog. Med. Virol. 34:89–128 (1987); and Burke, Virology 4:187–197 (1993), incorporated herein by reference). This is due at least partially to the fact that gB and gD are the most abundant HSV glycoproteins and therefore were the first glycoproteins to be expressed by recombinant technology, and to be shown to provide protection against HSV infection in animal models (Long et al., Infect. Immun. 37:761–764 (1984); Cantin et al., Proc. Natl. Acad. Sci. 84:590–5912 (1987); Eisenberg et al., J. Virol. 56:1014–1017 (1985); Pachl et al., J. Virol 61:315–325 (1987); and Straus et al., J. Infect. Dis. 167:1045–1052 (1993), incorporated herein by reference). Although immune responses to gD and gB play a major role in control of HSV-1 infection, (Cantin et al., Proc. Natl. Acad. Sci. 84:590–5912 (1987); Paoletti et al., Proc. Natl. Acad. Sci. 81:193–197 (1984); Cremer et al., Science 228:737–740 (1985); Martin et al., J. Immunol. 138:3431–3437 (1987). and Stanberry et al., J. Infect. Dis.

155:914–920 (1987), incorporated herein by reference), immune responses to gC, gE, and gI have also been shown to protect against primary infection (Ghiasi et al., J. Virol. 68:2142–2150 (1994), incorporated herein by reference). Although vaccination with gB alone or gD alone can completely protect against lethal challenge, protection against eye disease and the establishment of latency are not complete (Dix, Prog. Med. Virol. 34:89–128 (1987); Cremer et al., Science 228:737–740 (1985); Ghiasi et al., J. Virol. 68:2142–2150 (1994); Cantin et al., *Technological advances in vaccine development,* Alan R. Liss, Inc., 1988, p. 215–222; and Lasky et al., BioTech, 4:527–532 (1984), incorporated herein by reference). Similar results were reported using a mixture of gB+gD subunit vaccine (Stanberry et al., J. Infec. Dis. 155:914–920 (1987); Stanberry et al., Antiviral Research 11:203–214 (1989); and Stanberry et al., J. Gen. Virol. 70:3177–3185 (1989), incorporated herein by reference). In contrast, vaccination with live HSV-1 completely eliminated eye disease and significantly reduced the establishment of latency (Ghiasi et al., J. Virol. 68:2142–2150 (1994), incorporated herein by reference). Therefore, despite the fact that gB and gD elicited a significant protective response, the extent of this immunity was less than that which occurred following immunization with live or attenuated HSV-1 vaccines.

Our comparative analysis of individual HSV-1 glycoproteins has shown that gB and gD vaccines are less effective in controlling eye disease and latency than vaccination with live HSV-1 (Ghiasi et al., J. Virol. 68(4):2118–2126 (1994), incorporated herein by reference). This lack of a complete protective response against latency and eye disease highlights the need for an improved vaccine. We have deduced from these facts that the design of a vaccine consisting of a single or extremely limited numbers of epitopes (e.g., HSV glycoprotein D) may not be successful in prevention of eye disease and establishment of latency. We therefore hypothesized that an efficient vaccine may have to use a combination of these glycoproteins in order to induce a broader immune response to HSV-1 infection. Thus, to carry out comparative studies with live virus and gD, in this study have used mixtures of HSV-1 glycoproteins.

The ability of vaccination (prior to ocular challenge) with live HSV-1, but not any individual glycoprotein, to provide a better protection against the establishment of latency and eye disease may be due to: (1) replication of the live HSV-1 vaccine in the vaccinated mouse, or (2) the presence of many more potential protective epitopes in the live virus vaccine. To address the second possibility, we have examined the protective ability of mixtures of five, six, or seven expressed HSV-1 glycoproteins compared to that of gD, the most efficacious individual HSV-1 glycoprotein. The 7gP vaccine mixture contained the same total amount of HSV-1 glycoprotein (each of the 7 glycoproteins was present in 1/7th the amount of glycoprotein used for the gD vaccine). A PBS solution was used as a negative control (mock) vaccine, and live HSV-1 was used as a positive control vaccine. We have demonstrated that the mixture of 7 glycoproteins: (1) blocked viral replication in the eye more efficiently than gD, in a manner equivalent to live HSV-1 vaccine; (2) protected against eye disease more efficiently than gD, in a manner equivalent to live HSV-1 vaccine; and (3) protected against the establishment of HSV-1 latency more efficiently than gD, in a manner equivalent to live HSV-1 vaccine.

Various combinations and permutations of the seven HSV-1 glycoproteins or proteins can be made and used. Among these combinations include HSV-1 gD and gB, a combination of all seven HSV-1 glycoproteins in equimolar amounts, and any combination of one or more of the seven HSV-1 glycoproteins and proteins. Preferred embodiments include vaccines comprising four, five, six or seven HSV-1 glycoproteins, more preferably five, six, or seven HSV-1 glycoproteins, more preferably still a mixture of six or seven glycoproteins, and most preferably a mixture of seven glycoproteins. In all cases, it is desirable that the mixture include gB or gD, and more preferably both gB and gD. Particularly advantageous combinations include the mixtures (1) gB, gC, gD, gE, and gI; (2) gB, gC, gD, gE, gI and at least one of gG or gH; and (3) gB, gC, gD, gE, gI, gG, and gH.

Our previous studies have shown that of 7 HSV-1 glycoproteins (gB, gC, gD, gE, gG, gH, and gI) individually expressed in baculovirus, vaccination with gD provides the best protection against HSV-1 challenge. To determine if vaccination with a mixture of these 7 expressed glycoproteins could provide better protection against HSV-1 challenge than vaccination with gD alone, mice were vaccinated with a mixture of the 7 expressed glycoproteins or expressed gD alone. The amount of each of the 7 expressed glycoproteins in the mixture was equivalent to 1/7th the amount of gD used in the gD alone vaccination. Thus, the total amount of glycoprotein was the same for each vaccination.

For some parameters, such as neutralizing antibody titer, delayed type hypersensitivity (DTH), and survival following lethal challenge, no difference was observed between mice vaccinated with all 7 glycoproteins and those vaccinated with gD. Moreover, for other parameters, vaccination with all 7 glycoproteins appeared to provide better protection than vaccination with gD. Following ocular challenge, virus was not detected at any time in the tears of mice vaccinated with all 7 glycoproteins. In contrast, virus was detected in the tears of gD vaccinated mice for up to 3 days post challenge. Mock vaccinated mice had virus in their tears for as long as 10 days. Mice vaccinated with all 7 glycoproteins had no eye disease. while gD vaccinated mice had a significant amount of blepharitis. Finally, compared to gD vaccinated mice, the mice vaccinated with all 7 glycoproteins were more efficiently protected against the establishment of HSV-1 latency following ocular infection.

Our results therefore demonstrate that while for some protective parameters there was no significant difference between vaccination with gD or 7 glycoproteins, vaccination with 7 glycoproteins was more efficient in protecting challenged mice against some forms of eye disease, the duration of infection, and the establishment of latency.

With reference to our most preferred embodiment, we have used a mixture of seven major glycoproteins (gB, gC, gD, gE, gG, gH, and gI) as a subunit vaccine. We have shown that this mixture of 7 glycoproteins at 117 of the concentration of individual glycoprotein to: (1) completely block viral growth in the eye compared with gD; (2) completely protects against both short- and long-term eye disease compare to gD; (3) shows no tear Ig response before or after ocular challenge compared to gD; (4) shows a better protection against the establishment of HSV-1 latency than gD; and (5) has a similar overall protection to live HSV-1.

6. Adjuvants

MTP-PE is the adjuvant of choice for subconjunctival vaccinations. MTP-PE may be administered with the HSV-1 glycoproteins alone or in combination with other adjuvants. MTP-PE may also be encapsulated in a liposome in combination with one or more HSV-1 glycoproteins or proteins. The use of other adjuvants, known or yet to be discovered, however, is not foreclosed by the disclosure of MTP-PE as the preferred adjuvant.

For systemic vaccination, i.e. intramuscular (IM) or subcutaneous (SC) vaccination, the most powerful adjuvants may be used. These include, but are not limited to, alum, Freund's complete, Freund's incomplete, MTP-PE, ISCOMs (Quil A), and any combination of these.

EXAMPLE 1

Systemic Therapeutic Vaccination with recombinant HSV-2 gB-gD

Thirty-six NZW rabbits with culture proven binocular HSV-1 McKrae infection were given subcutaneous vaccinations (0.5 ml) of Chiron gB2 and gD2 with MTP-PE adjuvant on days 21 and 39 post infection. The mock vaccinated group received tissue culture media pursuant to the same schedule. Daily 7 day/wk swab cultires (primary rabbit kidney) were taken for 36 days beginning 3 weeks after the second vaccination. All positive cultures were confirmed by neutralization. ELISA titers (capture Ag purified KOS) were done on blood samples taken 5 weeks after the second vaccination (sera were diluted in ½ log steps from 1/100 to 1/300,000). Daily 5 day/wk slit lamp biomicroscopy was done over the same period.

TABLE 1

Spontaneous ocular shedding and dendritic positive eyes, following systemic vaccination

| Vaccine & Adjuvant | Route | # Animals/ # Eyes | + Culture | % Positive | # Dendritic | % Dentritic |
|---|---|---|---|---|---|---|
| Chiron gB2 + gD2 with MTP-PE | Subcutaneous | 19/38 | 124/1368 | 9.6% | 121/1140 | 1.93% |
| Mock without adjuvant | Subcutaneous | 17/34 | 151/1224 | 12.34% | 19/1020 | 1.86% |

*all eyes cultured for 36 consecutive days
**slit lamp biomicroscopy (5 days/wk) for 30 days As illustrated in Table 1, there is no significant difference in the number of positive cultures or the number of eyes with dendritic figures between the mock and the Chiron vaccinated groups. There is also no difference in (data not shown) (1) the number of eyes that have 1 or multiple recurrences; (2) the number of rabbits that have 1 or multiple recurrences; (3) the average duration of shedding events; (4) the severity of keratitis; or (5) the HSV-1 ELISA titer in high vs. low recurrence animals, although the average titer is slightly higher in the Chiron than the mock vaccinated group. There was no difference in long term scarring and no signs of ocular toxicity.

Although there was no increase in shedding or dendritic keratitis produced by systemic vaccination with gB2+gD2 with MTP-PE, neither was any significant decrease seen in the same parameters with the same systemic subunit vaccine. Consequently, systemic vaccination with gB plus gD does not produce adequate ocular protection from HSV-1 recurrences.

EXAMPLE 2

Systemic Vaccination with HSV-1 gD

V52, a genetically engineered vaccine virus recombinant that expresses the HSV-1 glycoprotein gD (obtained from B. Moss) was used to vaccinate rabbits intradermally. It should be noted, however, that the HSV-1 gD may also be obtained from the procedures described above or any equivalent. Significant HSV-1 neutralizing antibody titers were produced, although they were not as high as those induced by vaccination with live HSV-1. The mock vaccinated group received a vaccinia-influenza recombinant, V36. The positive control group received live attenuated HSV-1 virus (KOS) subcutaneously. Rabbits were challenged ocularly with topical application of $2\times10^5$ PFU of HSV-1 McKrae. Eyes were monitored for 35 days for epithelial keratitis, stromal keratitis, and iritis.

V52 gD provided a small amount of protection against HSV-1 induced epithelial keratitis (p=0.02) and long term stromal scarring (p=0.04). In addition, 89% of the V36 vaccinated rabbits (negative control) could be induced to reactivate. In contrast, only 55% of the V52 vaccinated rabbits could be induced to reactivate, suggesting a modest protective effect. The positive control rabbits vaccinated subcutaneously with KOS produced the same results as seen with gD. Hence, systemic vaccination with HSV-1 gD on live attenuated KOS HSV-1 did not produce adequate ocular protection from HSV-1 recurrences.

EXAMPLE 3

Local ocular vaccination with KOS

Twelve NZW rabbits were vaccinated with the non-pathogenic live HSV-1 strain, KOS. KOS replicates very well in the eye, however, even at extremely high titers, the KOS strain causes minimal eye disease in the rabbit. The rabbits were vaccinated by placing $5\times10^8$ virus in each eye and holding the eye closed for 30 seconds. A control group of 12 rabbits were each mock infected with tissue culture media. Four weeks later, the rabbits were challenged with HSV-1 McKrae and the eyes were observed by slit lamp biomicroscopy over a 2 week period. The severity of disease was scored on a scale of 0–4.

Maximum eye involvement occurred on day 7, the average severity of disease is shown in Table 2.

TABLE 2

Ocular vaccination protects against primary ocular infection

| | EYE Mock vaccinated | EYE KOS vaccinated | SYSTEMIC McKrae Vaccinated* |
|---|---|---|---|
| Epithelial keratitis | 1.4 ± 0.5 | 0.0 | 2.1 ± 1.2 |
| Stromal keratitis | 2.0 ± 0.5 | 0.0 | 1.9 ± 1.0 |
| Iritis | 2.1 ± 1.7 | 0.1 ± 0.05 | 1.5 ± 1.4 |

*McKrae data is from the V52 experiment described above.

As demonstrated above, the protection afforded against ocular challenge at 4 weeks was almost complete. Ocular vaccination was dramatically more efficient than the systemic vaccination demonstrated in Examples 1 and 2 above. This experiment therefore suggests that a local ocular vaccine may afford the necessary protection in the rabbit against ocular challenge that is lacking with systemic vaccination. Moreover, since ocular vaccination appears more powerful in protecting against primary ocular infection, it follows then that it is also likely to be more powerful in protecting against ocular recurrence. Because the rabbit ocular model of HSV infection mimics the human infection, local ocular vaccination also appears to represent the best protection from HSV-1 ocular recurrences in humans.

EXAMPLE 4

Local Ocular Vaccination with Expressed HSV-1 gB and gD

Five NZW rabbits with culture proven binocular HSV-1 McKrae infection were given subconjunctival vaccinations on days 32 and 54 post infection. The vaccine comprised equal amounts of expressed gB1 and gD1 mixed 50/50 with MTP-PE adjuvant. Nine eyes were vaccinated: 4 animals bilateral, 1 unilateral. Daily 7 day/wk swab cultures (primary rabbit kidney) were taken for 22 days beginning 3 weeks after the second vaccination. All positive cultures were confirmed by neutralization. Daily 5 day/wk slit lamp biomicroscopy was carried out over the same period.

There were no corneal or anterior chamber abnormalities seen on biomicroscopy that differed from the mock vaccinated animals. All eyes showed mild generalized injection for 1 week following subconjunctival vaccination. Three eyes showed sustained localized mild conjunctival injection at the vaccination site.

The results shown in Table 3 below are intriguing and suggest reduced shedding following ocular subconjunctival vaccination with gB1+gD1. These experiments demonstrate that (1) local conjunctival vaccination is possible without apparent harm to the recipients; and (2) local ocular vaccination is more effective then systemic vaccination in preventing HSV ocular recurrences.

in humans in the United States and a major cause of viral induced blindness in the world.

EXAMPLE 5

Improved Protection Against HSV Challenge Using a Mixture of Seven Expressed HSV-1 Glycoproteins (gB, gC, gD, gE, gG, gH, and gI)

Virus and cells. Plaque purified HSV-1 strains were grown in CV-1 cell monolayers in minimal essential media (MEM) containing 10% fetal calf serum as we previously described (Wechsler et al., J. Virol. 62:4051–5048 (1988), incorporated herein by reference). McKrae, a stromal disease causing, neurovirulent, HSV-1 strain was the challenge virus. KOS, a nonneurovirulent nonstromal disease producing strain was the positive control vaccine. Baculovirus recombinants were grown in Sf9 cells using TNM-FH media containing 10% fetal bovine serum as previously described (Ghiasi et al., Arch. Virol. 121:163–178 (1991), incorporated herein by reference).

Immunization of mice. Sf9 cells were infected with 10 PFU of recombinant baculovirus expressing either gB, gC, gD, gG, gE, gH, or gI (Ghiasi et al., Arch. Virol. 121:163–178 (1991); Ghiasi et al., Virology 185:187–194 (1991); Ghiasi et al., Virus Res. 22:25–39 (1992); Ghiasi et al., J. virol. 66:2505–2509 (1992); Ghiasi et al., J. Gen. Virol. 73:719–722 (1992); Ghiasi et al., Antiviral Research 18:291–302 (1992); Ghiasi et al., Virology 188:469–476 (1992); and Ghiasi et al., Virology 190:233–239 (1992), incorporated herein by reference). The infected Sf9 cells were harvested 72 hr post infection, washed, suspended in PBS, and combined with adjuvant at a 1:1 ratio before vaccination. The amount of each expressed glycoprotein was estimated by commassie blue staining of SDS-PAGE of infected Sf9 cell extracts. gD vaccinations contained approximately 7 micrograms of gD. The mixture of all 7 glycoproteins (7gP) contained approximately 1 microgram of each expressed glycoprotein per vaccination. Six to eight

TABLE 3

Spontaneous ocular shedding and dendritic keratitis following local subconjunctival vaccination with baculovirus expressed HSV-1 gB and gD

| Vaccine & Adjuvant | Route | # Animals/ # Eyes | + Culture | % Positive | # Dendritic | Dentritic |
|---|---|---|---|---|---|---|
| gB1 + gD1 with MTP-PE | Local Subcutaneous | 5/9 | 9/198 | 4.55% | 2/126 | 1.59% |
| KOS without adjuvant | Local Subcutaneous | 17/34 | 75/748 | 10.02% | 11/476 | 2.31% |

*all eyes cultured for 22 consecutive days; KOS numbers are reported for the days that the subconjunctival animals were cultured, i.e., Days 77–99 post infection.
**slit lamp biomicroscopy (5 days/wk) for 14 days In summary, the Examples above illustrate that: 1) systemic vaccination with HSV-2 gB+gD with MTP-PE did not produce adequate ocular protection from HSV-1 recurrences; 2) systemic vaccination with HSV-1 gD or live attenuated KOS HSV-1 also did not produce adequate ocular protection from HSV-1 recurrences; 3) local ocular vaccination with a live nonpathogenic HSV-1 strain did protect against primary ocular infection; and 4) local ocular vaccination with HSV-1 gB and gD was effective in preventing HSV ocular recurrences. These examples illustrate that a local ocular immunogenic comprised of one or more HSV-1 glycoproteins or proteins, would greatly alleviate HSV ocular recurrences, the most frequent serious viral eye infection week-old female BALB/c mice were vaccinated both subcutaneously (sc) and intraperitoneally (ip). SC injections were done using Freund's complete adjuvant on day 0 and an identical preparation but with Freund's incomplete adjuvant on days 21 and 42. IP injections were done on the same days with the same amount of glycoprotein in PBS. The mock vaccinated mice were similarly inoculated with PBS. Positive control mice were vaccinated ip only on the same schedule with $2 \times 10^5$ pfu of live HSV-1 (strain KOS).

Delayed type hypersensitivity (DTH). DTH response to 7gP was measured as we described previously (Ghiasi et al., J. of Virol. 68:2142–2150 (1994), incorporated herein by reference). Controls included HSV-1 (strain KOS) vaccinated mice, baculovirus expressed gD vaccinated mice, PBS (mock) vaccinated mice.

Serum neutralizing antibody titers were determined by 50% plaque reduction assays as we described previously (Ghiasi et al., Arch. Virol. 121:163–178 (1991), incorporated herein by reference) using sera collected 3 weeks after the first and the third vaccination.

Ocular challenge was done 3 weeks after the final vaccination. $2 \times 10^5$ (10 LD50) PFU of HSV-1 strain McKrae in 5 microliters of tissue culture media was placed in each eye without corneal scarification and the lid gently rubbed for 30 sec. The challenged mice were monitored for a period of four weeks.

IP challenge. Three weeks after the third (final) vaccination, mice were challenged intraperitoneally with $2 \times 10^6$ (4 LD50) or $2 \times 10^7$ (40 LD50) of HSV-1 (strain McKrae). The challenged mice were monitored for a period of two weeks.

Monitoring eye disease. The severity of ocular disease was scored on a 0 to 4 scale in a masked fashion by examination with slit lamp biomicroscope using 1% fluorescein. A score of 0 indicates no eye disease while a score of 4 indicates a high level of eye disease (Nesburn et al., Invet. Ophthal. Vis. Sci. 31:77–82 (1990) and Ghiasi et al., Invest. Ophthal. Vis. Sci. (In press) (1995), incorporated herein by reference). Eyes were examined on days 1, 3, 7, 14, 21 and 28.

Virus replication in mouse eyes. Following vaccination and ocular challenge, the mouse eyes were swabbed with a nylon swab and the swabs were transferred to a culture tube containing 0.5 ml of media (Ghiasi et al., Invest. Ophthal. Vis. Sci. (In press) (1995), incorporated herein by reference). 0.1 ml aliquots were plated on CV-1 indicator cells and the cells were observed for the development of HSV-1 cytopathic effects. Six eyes (from 3 mice) were scored as positive or negative for HSV-1 from each group on days 1, 2, 3, 4, 5, 7, 10, and 14.

Detection of virus and immunoglobulin (Ig) in the tear of vaccinated mice. Eyes from 3 mice (6 eyes) vaccinated three times and challenged ocularly as described above were swabbed. The swabs were transferred to a culture tube containing 0.5 ml of media. The presence of HSV-1 in the eye on days 1, 2, 3, 4, 5, 7, 10, and 14 was determined by titration of 100 microliters of tear films using a confluent monolayer of CV-1 cells In 96-well plates as described previously. Also, the relative amounts of immunoglobulin (IgG1, IgG2a, IgG2b, IgG3, IgM, and IgA) in the tear of vaccinated mice were determined on days 0, 7, 14, and 21 post challenge using monoclonal mouse isotyping kit (Pharmingen, San Diego, Calif.).

Determination of latency. Mice surviving 28 days after challenge were euthanized. Both trigeminal ganglia were removed and individually explanted onto RS (rabbit skin) cell monolayers. The monolayers were monitored for 30 days for the presence of infectious virus (HSV-1 cytopathic effects).

Statistical analysis. Protective parameters were analyzed by the Student's t test and Fisher's exact test using Instat, a personal computer program (available from GraphPad Software V2.02). Results were considered statistically significant when the "p" value was <0.05.

Figure 7:
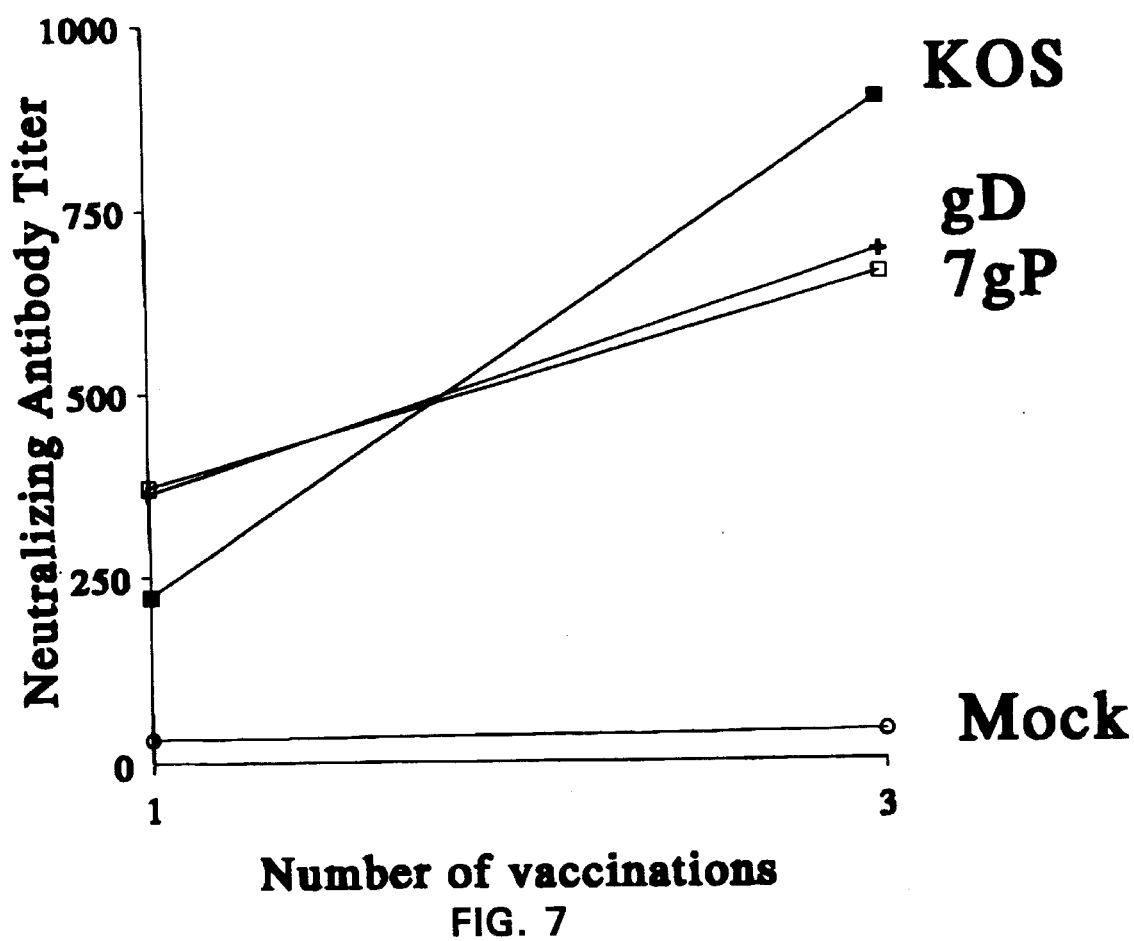
FIG. 7 shows neutralizing antibody titers in mice vaccinated with 7gP. Five mice/group from the 1× or 3× vaccinated mice shown in Table 1, were bled just prior to challenge. HSV-1 neutralizing antibody titers were determined for each serum as described in Example 5. For each bar, the neutralizing antibody titer (Y-axis) represents the average of the titers from 5 sera. The 7gP neutralizing antibody titers were significantly different from mock controls ($p<0.05$, Fisher's Exact test), but similar to gD or KOS ($p>0.05$).

RESULTS: Induction of HSV-1 neutralizing antibody titers. Groups of 10 BALB/c mice were vaccinated one or three times as described above. Three weeks after the first vaccination and three weeks after the third vaccination, sera were collected from 5 vaccinated mice per group. The individual sera were heat-inactivated for 30 min. at 56 C., and neutralization titers were determined by a 50% plaque reduction assay (FIG. 7). Although the neutralizing antibody titer for the KOS vaccinated mice appeared slightly lower following one vaccination and slightly higher following three vaccinations, these differences were not significant (p>0.1, Student t test). In contrast, compared to the mock vaccinated mice, all three groups had higher neutralizing antibody titers at both times (p<0.01).

Protection of vaccinated mice from lethal ocular challenge. Three weeks after the third vaccination, the vaccinated mice described above were challenged binocularly with $2 \times 10^5$ PFU of HSV-1 strain McKrae (LD50=10/eye) (Table 4, left side). Ten of ten mice (100%) survived the lethal challenge in the groups vaccinated with 7gP, gD, and KOS. In contrast, only 2 of 10 (20%) mock vaccinated mice survived the lethal challenge. The protection provided by 7gP, gD, or KOS was statistically significant compared to the mock vaccinated mice (p=0.0004, Fisher's exact test).

TABLE 4

Survival of mice vaccinated with a mixture of 7gP following lethal ocular challenge[a]

| | Number of vaccinations[b] | | | |
|---|---|---|---|---|
| | Three vaccinations | | One vaccination | |
| Antigen | Survival/Total | % Survival | Survival/Total | % Survival |
| 7gP | 10/10[c] | 100 | 10/10[c] | 100 |
| gD | 10/10[c] | 100 | 10/10[c] | 100 |
| KOS | 10/10[c] | 100 | 10/10[c] | 100 |
| Mock | 2/10 | 20 | 2/10 | 20 |

[a]Mice were vaccinated once or three times and challenged ocularly with $2 \times 10^5$ of McKrae as described in Example 5.
[b]Survival was followed for 4 weeks.
[c]Statistically significant compared to mock group (Fisher's exact test, p = 0.0004).

Since following three vaccinations both the gD and the 7gP were completely protected against death, we next examined protection following a single vaccination. Mice were vaccinated once rather than three times and challenged as above. Again, all the mice except those in the mock vaccinated group were completely protected (Table 4, right side).

Protection of vaccinated mice from lethal ip challenge. To determine if either higher challenge doses or ip rather than ocular lethal challenge would allow us to differentiate between protection by vaccination with 7gP versus gD, a second set of experiments was done. As before, mice were vaccinated three times with 7gP, gD, KOS, or the mock vaccine. Ten mice per group were then challenged ip with either $2 \times 10^6$ PFU/mouse (4 LD50) or $2 \times 10^7$ PFU/mouse (40 LD50) of HSV-1 McKrae. Only 2 of 10 mock vaccinated mice challenged with $2 \times 10^6$ pfu of McKrae and 0 of 10 mice challenged with $2 \times 10^7$ pfu of McKrae survived (Table 5). In contrast, as seen following ocular challenge above, 100% of the mice vaccinated with 7gP, gD, and KOS survived both lethal challenge doses (Table 5) (p<0.001, Fisher's exact test). Therefore, even at the highest challenge dose used, vaccination with 7gP completely protected mice against lethal HSV-1 challenge.

TABLE 5

Survival of mice vaccinated with a mixture of 7gP following lethal ip challenge[a]

| Antigen | $2 \times 10^6$ PFU/Mouse Survival/Total | $2 \times 10^7$ PFU/Mouse Survival/Total |
| --- | --- | --- |
| 7gP | 10/10 (100%)[b] | 10/10 (100%)[b] |
| gD | 10/10 (100%)[b] | 10/10 (100%)[b] |
| KOS | 10/10 (100%)[b] | 10/10 (100%)[b] |
| Mock | 2/10 (20%) | 0/10 (0%) |

[a]Mice were vaccinated three times and then challenged ip with either $2 \times 10^6$ PFU/mouse or $2 \times 10^7$ PFU/mouse of HSV-1 as described in Example 5.
[b]Statistically significant compared to mock group (p < 0.001, Fisher's exact test).

Effect of vaccination an the establishment of latent infection. Vaccinated and mock vaccinated mice that survived ocular challenge were sacrificed 28 days post infection to determine the percentage of mice in which latency had been established. Both trigeminal ganglia (TGs) were removed from each mouse and individually analyzed for the presence of latent HSV-1 by explant co-cultivation as described above. Following ocular challenge of mice receiving a single vaccination (Table 6), 100% (4/4) of the TGs from the surviving mock vaccinated mice became latently infected. In contrast, only 2/20 (10%) of the TGs from the 7gP vaccinated mice became latently infected. This was significantly less than the mock group (p<0.002, Fisher exact test) and identical to the KOS vaccinated group (2/20; 10%). The gD vaccinated group also showed protection against the establishment of latency (4/20; 20%; p=0.007 versus mock), but this was not statistically different from the 7gP group (p=0.7).

TABLE 6

Protection against establishment of latency in mice vaccinated with a mixture of 7gP following lethal ocular challenge

| | Latency* | |
| --- | --- | --- |
| Antigen | One vaccination Latent TG/Total TG | Three vaccinations Latent TG/Total TG |
| 7gP | 2/20 (10%) | 0/20 (0%) |
| gD | 4/20 (20%) | 4/20 (20%) |
| KOS | 2/20 (10%) | 0/20 (0%) |
| Mock (PBS) | 4/4 (100%) | 4/4 (100%) |

*Mice vaccinated 1 or 3 times as described in Example 5 and challenged ocularly. 28 days post challenge, the surviving mice were sacrificed and their trigeminal ganglia were analyzed for the presence of latent virus as described in Example 5.

Following ocular challenge of mice vaccinated three times, the number and percent of TGs in which latency was established was unchanged in the mock (4/4; 100%) and gD vaccinated groups (4/20; 20% latency). However, the 7gP vaccinated mice and the KOS vaccinated mice were now completely protected against the establishment of latency (0/20 TGs for each group; p<0.0001 versus mock). Thus, 7gP vaccination provided protection against the establishment of latency that was comparable to that provided by KOS.

In both experiments there was a trend towards more efficacious protection against the establishment of latency by 7gP compared to gD. However, neither trend was statistically significant (p>0.1). However, since the results following one or three vaccinations were so similar, it was possible to combine them to increase the statistical power. Analysis of the combined data indicated that vaccination with 7gP provided significantly more protection against the establishment of latency than vaccination with gD (2/40 latent TGs versus 8/40 latent TGs; p=0.04, Fisher's exact test, single sided).

Quantitation of eye disease. To examine protection against eye disease, 10 mice per group were vaccinated 3 times and challenged ocularly as above. All 20 eyes/group were examined on days 1, 3, 7, 14, 21, and 28 and scored on a 0 to 4 scale for eye disease as described above. The peak amounts of blepharitis (day 7), neovascularization (day 21), and keratitis (day 28) are shown in Table 7. Vaccination with gD and 7gP each provided complete protection against neovascularization and keratitis, as did vaccination with KOS. As expected, the mock vaccinated mice had significantly more neovascularization and keratitis (p<0.0001, Student t test).

TABLE 7

Peak levels of blepharitis, neovascularization, and keratitis in mice immunized with a mixture of 7gP following lethal ocular challenge.[a]

| | Eye Disease | | |
| --- | --- | --- | --- |
| Antigen | Blepharitis | Neovascularization | Keratitis |
| 7gP | 0 | 0 | 0 |
| gD | $0.6 \pm 0.2$[b] | 0 | 0 |
| KOS | 0 | 0 | 0 |
| Mock | $2.8 \pm 0.3$ | $1.5 \pm 0.8$ | $1.3 \pm 0.3$ |

[a]Mice were vaccinated three times and challenged ocularly. Eye disease was scored on a 0 to 4 scale as described in Example 5.
[b]Statistically significant compared to 7gP group (p < 0.006, Student's t test).

Differences between gD and 7gP vaccination are found for blepharitis (Table 7). Although the gD vaccinated mice were partially protected against blepharitis (they had significantly less blepharitis than the mock vaccinated mice, p<0.001, Student t test), the gD vaccinated mice had significantly more blepharitis than the 7gP vaccinated mice (p=0.006). Thus, vaccination with 7gP appeared to be more efficacious than vaccination with gD in protecting against at least one form of HSV-1 induced eye disease.

Local replication. Three mice per group (6 eyes/group; 4 eyes for mock group after day 10 due to death) were vaccinated three times and challenged binocularly as described above. Tear films were collected on days 1, 2, 3, 4, 5, 7, 10, and 14 post challenge and cultured for the presence of infectious virus (Table 8). In the mock vaccinated group, virus was detected in 2 to 4 eyes through day 10 post infection. In the gD vaccinated group virus was found in four eyes on day 2 and in three eyes on day 3 post challenge. In contrast. no eyes from 7gP or KOS vaccinated mice had any detectable virus at any time (Table 8). The difference between the 7gP and gD vaccinated eyes was statistically significant (p=0.003, Fisher's exact test). Thus, vaccination with 7gP was more efficacious at eliminating virus growth in the eyes than was vaccination with gD.

TABLE 8

| Detection of virus in eyes of mice vaccinated with a mixture of 7gP following ocular challenge.[a] | | | | | | | | |
|---|---|---|---|---|---|---|---|---|
| | Days after ocular challenge[b] | | | | | | | |
| Antigen | 1 | 2 | 3 | 4 | 5 | 7 | 10 | 14 |
| 7gP | 0/6 | 0/6 | 0/6 | 0/6 | 0/6 | 0/6 | 0/6 | 0/6 |
| gD | 0/6 | 4/6[c] | 3/6[c] | 0/6[c] | 0/6 | 0/6 | 0/6 | 0/6 |
| KOS | 0/6 | 0/6 | 0/6 | 0/6 | 0/6 | 0/6 | 0/6 | 0/6 |
| Mock | 2/6 | 3/6[c] | 4/6[c] | 4/6[c] | 4/6[c] | 2/6 | 2/4 | 0/4 |

[a]Mice were vaccinated three times and challenged ocularly as described in Example 5.
[b]The presence of virus in eyes of challenged mice were determined by titration of tear films from 3 specific mice in 7gP, gD, and KOS challenged mice. While in the mock group, the sampling after day 10 was done on surviving mice as described in Example 5.
[c]Statistically significant compared to 7gP group ($p = 0.03$, Fisher's exact test, single sided).

Effect of Vaccination on Tear Ig production. To establish a possible-correlation between virus growth in the eye and local Ig production, tears collected as above were used to measure tear IgA, IgM, IgG1, IgG2a, IgG2b, and IgG3 (Table 9). Neither groups showed any Ig activities before ocular challenge. Similarly after ocular challenge, 7gP or KOS groups showed no tear IgA, IgM, IgG1, IgG2a, IgG2b, or IgG3 (Table 9). In contrast to 7gP, gD vaccinated mice showed tear IgA, IgG1, IgG2a, IgG2b, and IgG3 up to day 14 post challenge. The differences between 7gP and gD vaccinated tear Ig were statistically significant ($p<0.05$, Student's t test). Mock group had the highest level as well as the longest duration of tear IgA, IgM, IgG1, IgG2a, IgG2b, and IgG3. Thus, 7gP and KOS groups showed no tear IgA, IgM, or IgG1, IgG2a, IgG2b, and IgG3 activities prior to or after ocular challenge, while gD group showed IgA and IgG activities. Mock group had the highest tear IgA, IgM and IgG.

TABLE 9

| Detection of tear IgA, IgM, IgG1, IgG2a, IgG2b, and IgG3 in eyes of mice vaccinated with a mixture of seven recombinant baculoviruses expressing HSV-1 glycoproteins (gB, gC, gD, gE, gG, gH, and gI) following ocular challenge.[a] | | | | | | | |
|---|---|---|---|---|---|---|---|
| Antigen | Day | IgA | IgM | IgG1 | IgG2a | IgG2b | IgG3 |
| 7gP | 0 | 0 | 0 | 0 | 0 | 0 | 0 |
| | 7 | 0 | 0 | 0 | 0 | 0 | 0 |
| | 14 | 0 | 0 | 0 | 0 | 0 | 0 |
| | 21 | 0 | 0 | 0 | 0 | 0 | 0 |
| KOS | 0 | 0 | 0 | 0 | 0 | 0 | 0 |
| | 7 | 0 | 0 | 0 | 0 | 0 | 0 |
| | 14 | 0 | 0 | 0 | 0 | 0 | 0 |
| | 21 | 0 | 0 | 0 | 0 | 0 | 0 |
| gD | 0 | 0 | 0 | 0 | 0 | 0 | 0 |
| | 7 | .20 ± .04 | 0 | .47 ± .15 | .65 ± .23 | .47 ± .19 | .29 ± .11 |
| | 14 | .16 ± .03 | 0 | 0 | .23 ± .10 | .18 ± .10 | 0 |
| | 21 | 0 | 0 | 0 | 0 | 0 | 0 |
| Mock | 0 | 0 | 0 | 0 | 0 | 0 | 0 |
| | 7 | .15 ± .03 | .24 ± .09 | .38 ± .10 | 1.04 ± .29 | 1.34 ± .23 | .41 ± .14 |
| | 14 | .12 ± .09 | .19 ± .04 | .35 ± .09 | .98 ± .15 | .87 ± .09 | .37 ± .09 |
| | 21 | .42 ± .21 | .17 ± .11 | .35 ± .12 | .93 ± .41 | .85 ± .42 | .30 ± .18 |

[a]Mice were vaccinated three times and challenged ocularly as described in Example 5. The presence of Ig in the tear was determined from the eyes of 3 specific mice in 7gP, gD, and KOS vaccinated mice, while in the mock group the sampling after day 10 was done on the eyes of surviving mice as described in Example 5.
[b]Differences between 7gP and gD were statistically significant ($p < 0.03$, Student's t test).

In summary, we have previously constructed recombinant baculoviruses expressing high levels of each of the first seven reported HSV-1 glycoproteins (gB, gC, gD, gE, gI, gG, and gH) in insect cells (Ghiasi et al., J. Virol. 68:2142–2150 (1994), incorporated herein by reference). Comparative studies employing these expressed glycoproteins as vaccines to protect mice against ocular or ip challenge with HSV-1 allowed these glycoproteins to be ranked gD>gB>gC=gE=gI>gG>gH as to their overall efficacy (Ghiasi et al., J. Virol. 68:2142–2150 (1994), incorporated herein by reference). Those studies also showed that the best correlation between efficacy and vaccine induced immune responses was to neutralizing antibody titers. There was no correlation between protection and DTH or lymphocyte proliferation responses. In the above studies (Ghiasi et al., J. Virol. 68:2142–2150 (1994), incorporated herein by reference) gD was the most efficacious individual glycoprotein vaccine for protection against death, eye disease, virus replication in the eye, and the establishment of latency. However, except for protection against death, none of the individual glycoproteins, including gD, was as efficacious as vaccination with the live, avirulent virus strain KOS.

Because our previous comparative studies indicated that no individual glycoprotein vaccine gave maximum protection (as minimally defined by the protection provided by KOS vaccine) (Ghiasi et al., J. Virol. 68:2142–2150 (1994), incorporated herein by reference), we have sought to develop improved vaccine compositions for HSV-1. We have discovered that a mixture of all seven expressed glycoproteins produces better protection than the best individual glycoprotein, gD. To ensure that 7gP did not induce better protection than gD simply due to the use of more total HSV-1 glycoprotein in the vaccine, each 7gP vaccine inoculation contained the same total amount of HSV-1 glycoprotein that was used for gD. Thus, each of the expressed glycoproteins in the 7gP vaccine was present in 1/7th the concentration of gD in the gD vaccine. The gD vaccine contained approximately 7 micrograms of gD per inoculation. The 7gP vaccine contained approximately 1 microgram of each of the 7 glycoproteins per inoculation.

For some protective parameters we found that the gD vaccine and the 7gP vaccine had similar efficacy. For example, the 7gP vaccine and the gD vaccine induced similar HSV-1 neutralizing antibody titers, and these were similar to the level induced by vaccination with live KOS. With both the high and low challenge doses employed here, and independent of whether the route of challenge was ocular or ip, the gD and the 7gP vaccines both protected 100% of the mice against death. Again this was the same as the KOS vaccine.

In contrast, for other important parameters the 7gP vaccine was more efficacious than gD alone. Similar to the KOS vaccination results, 7gP vaccination appeared to completely prevent virus replication in the eye following ocular challenge. gD, on the other hand, although providing protection compared to mock vaccination, allowed significant amounts of ocular virus replication. We also found that while vaccination with 7gP (like KOS) resulted in no detectable eye disease, mice vaccinated with gD developed a moderate, but significant, amount of blepharitis. Furthermore, using an ELISA system, we have demonstrated that mice vaccinated with KOS or 7gP showed no tear Ig response, while gD vaccinated mice showed IgA, IgG1, IgG2a, IgG2b, and IgG3 in their tear after ocular challenge. The pattern of protection from latency and eye disease with 7gP was similar regardless of whether mice were vaccinated once or three times. Perhaps most importantly, vaccination with 7gP produced better protection against the establishment of latency than did gD vaccination. Following three vaccinations no latency was detected in any of the 7gP vaccinated mice. This protection was identical to that seen with the positive control KOS vaccination. Since protection against the establishment of latency is arguably the most clinically important protective parameter for a prophylactic herpes vaccine for human use, our results clearly demonstrate that a cocktail of expressed viral glycoproteins is a better subunit vaccine than any individual glycoprotein.

In conclusion, our results demonstrate that a mixture of seven expressed HSV-1 glycoproteins is a more effective subunit vaccine against HSV-1 infection than vaccination with individual glycoprotein, despite the fact that the concentration of each glycoprotein in this cocktail was only $1/7$ of the dose that we had used for individual glycoprotein vaccination. Thus, in this study, by using a mixture of 7 glycoproteins, we have been able to completely eliminate eye disease and virus growth in the eye as well as to reduce trigeminal latency to 5%. Consequently, our results indicate that a cocktail of gB, gC, gD, gE, gG, gH, and gI is a better subunit vaccine to control latency and eye disease, than any individual glycoprotein alone. Finally we note that, while we have used in this study a 1:1 ratio of glycoproteins in our vaccine, adjustments of this ratio to create other effective vaccines is a matter within the skill of the art, and accordingly these other vaccines are within the scope of the present invention.

EXAMPLE 6

Improved Protection Against HSV Challenge Using a Mixture of Five or Six Expressed HSV-1 Glycoproteins In accordance with the procedures set forth in Example 5, vaccines comprising a mixture of five glycoproteins including gB, gC, gD, gE, and gI, and vaccines including as a sixth glycoprotein either gG or gH are formulated and tested for efficacy by comparison to gD alone, 7gP vaccine, and KOS. The 5gP formulations include each glycoprotein at $1/5$ the concentration of the gD formulation, while 6gP formulations include each glycoprotein at $1/6$ the concentration of the gD formulation, such that a comparison of protection is made between vaccines having equivalent overall glycoprotein concentrations. The 5gP and 6gP vaccines are tested for effect on the establishment of latent infection, quantitation of eye disease, virus replication in mouse eyes, protection of mice from lethal HSV challenge, and induction of neutralizing antibody titers using procedures set forth in Example 5 above. As set forth in Tables 1 and 2 for 7gP vaccines, the 6gP and 5gP vaccines show a 100% survival rate for one and three vaccinations. Studies on the protection against establishment of latency show that for 5gP and 6gP vaccines, on one vaccination, 2–4/20 mice show latent virus in their trigeminal ganglia, while on three vaccinations, 0/20 mice show latent virus. Moreover, the peak levels of blepharitis, neovascularization, and keratitis are all 0 for mice vaccinated with 5gP, 6gP, or 7gP vaccines. Finally, 0/6 mice show any detectable virus in their eyes following vaccination with 5gP, 6gP, or 7gP vaccines after ocular challenge with HSV-1. These results indicate that 5gP and 6gP vaccines have similar efficacy for protection against HSV-1 infection as demonstrated for the 7gP vaccine.

The foregoing detailed description is given for clearness of understanding only, and no unnecessary limitations are to be understood or inferred therefrom, as modifications within the scope of the invention will be obvious to those skilled in the art.

We claim:

1. A pharmaceutical composition comprising individually expressed Herpes Simplex Virus-1 (HSV-1) glycoproteins gB, gC, gD, gE, gG, gH and gI.

2. The composition of claim 1, wherein the HSV-1 glycoproteins are expressed in a baculovirus.

3. The composition of claim 1, further comprising at least one adjuvant.

4. The composition of claim 3, wherein the adjuvant is selected from the group consisting of alum,
M-acetylmuramyl-L-alanyl-B-isoglutaminyl-L-alanine-2-(1'-2'-dipalmitoyl-sn-glycerol-3-hydroxyphosphoryloxy)-ethylamine, and liposomes.

5. A pharmaceutical composition consisting essentially of:
herpes simplex virus-1 (HSV-1) glycoproteins gB, gC, gD, gE, gG, gH, and gI separate from HSV-1 virus; and a pharmaceutically acceptable adjuvant.

6. The composition of claim 5, wherein the adjuvant is selected from the group consisting of selected from the group consisting of alum, M-acetylmuramyl-L-alanyl-B-isoglutaminyl-L-alanine-2-(1'-2'-dipalmitoyl-sn-glycerol-3-hydroxyphosphoryloxy)-ethylamine, and liposomes.

7. A method for treating herpes simplex virus-1(HSV-1) infection, said method comprising the step of inoculating a host with the composition defined in claim 5.

8. A pharmaceutical composition comprising individually expressed herpes simplex virus-1 (HSV-1) glycoproteins gB, gC, gD, gE, and gI.

9. The composition of claim 8, further comprising at least one of HSV-1 glycoproteins gG and gH.

10. The composition of claim 9, wherein at least one of glycoproteins gG and gH is produced in a baculovirus.

11. The composition of claim 8, further comprising at least one adjuvant.

12. The composition of claim 11, wherein the adjuvant is selected from the group consisting of selected from the group consisting of alum, M-acetylmuramyl-L-alanyl-B-isoglutaminyl-L-alanine-2-(1'-2'-dipalmitoyl-sn-glycerol-3-hydroxyphosphoryloxy)-ethylamine, and liposomes.

* * * * *